(12) United States Patent
De Waal Malefyt et al.

(10) Patent No.: US 8,475,793 B2
(45) Date of Patent: Jul. 2, 2013

(54) ENGINEERED ANTI-TSLPR ANTIBODIES

(75) Inventors: Rene De Waal Malefyt, Sunnyvale, CA (US); Leonard G. Presta, San Francisco, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 55 days.

(21) Appl. No.: 12/863,839

(22) PCT Filed: Feb. 6, 2009

(86) PCT No.: PCT/US2009/033383
§ 371 (c)(1),
(2), (4) Date: Sep. 21, 2010

(87) PCT Pub. No.: WO2009/100324
PCT Pub. Date: Aug. 13, 2009

(65) Prior Publication Data
US 2011/0020369 A1    Jan. 27, 2011

Related U.S. Application Data

(60) Provisional application No. 61/026,833, filed on Feb. 7, 2008, provisional application No. 61/042,030, filed on Apr. 3, 2008.

(51) Int. Cl.
*A61K 39/395* (2006.01)
*C07K 16/18* (2006.01)
*C07K 16/28* (2006.01)

(52) U.S. Cl.
USPC .......... 424/133.1; 424/135.1; 424/143.1; 424/152.1; 424/153.1; 424/172.1; 424/173.1; 424/800; 424/801; 424/805; 530/387.3; 530/388.22; 530/388.7; 530/808; 530/866; 530/867

(58) Field of Classification Search
None
See application file for complete search history.

(56) References Cited

FOREIGN PATENT DOCUMENTS

| WO | WO 2002/00724 | 1/2002 |
|----|---------------|--------|
| WO | WO 2006/023791 | 3/2006 |
| WO | WO 2007/112146 | 10/2007 |
| WO | WO 2008/155365 | 12/2008 |

OTHER PUBLICATIONS

Nguyen, K. et al., TSLP Directly Inhibits IL-10 Expression by Human Regulatory T Cells, Journal of Allergy and Clinical Immunology, vol. 121, No. 3, p. 791 (2008).
Shi, L., et al., "Local blockade of TSLP receptor alleviated allergic disease by regulating airway dendritic cells", Clinical Immunology, vol. 129, No. 2, pp. 202-210 (2008).
Anonymous: "Anti-mouse TSLP R Antibody", R&D Systems Inc., pp. 1-2 (2007).
Rosenqvist, L., et al., "Soluble thymic stromal lymphopoietin receptors are absent in murine sera-detection with anti-mTSLPR monoclonal antibodies", ACTA Pathologica, Microbiologica, ET Immunologica Scandinavica, vol. 113, No. 5, pp. 324-331 (2005).
Jiang, Q, et al., "Delayed functional maturation of natural regulatory T cells in the medulla of postnatal thymus: role of TSLP", BMC Immunology, vol. 7, No. 6, pp. 1-14 ((2006).
Al-Shami, A., et al., "A role for TSLP in the development of inflammation in an asthma model", The Journal of Experimental Medicine, vol. 202, No. 6, pp. 829-839 (2005).

*Primary Examiner* — Ronald Schwadron
(74) *Attorney, Agent, or Firm* — Gloria M. Fuentes; Patricia L. Chisholm; Immac J. Thampoe

(57) ABSTRACT

The invention relates to binding compounds that specifically bind to human TSLPR, as well as uses thereof, e.g., in the treatment of inflammatory disorders.

4 Claims, 5 Drawing Sheets

FIGURE 1A

```
mu13H5  QVLLKQSGPSIVQPSQSLSITCTVS GFSLSRYGVH WVRQSPGKGLEWLG
        *  ***   ***  ****           **********   *  ********
hu13H5  QVQLVESGGVVQPGRSLRLSCAAS GFSLSRYGVH WVRQAPGKGLEWVA mu13H5  VIWRSGSTDYNAAFMS RLSITQDNSKSQVFFNMNSLQSDDSAIYYCAK
        **************   *     *******        *  *   *
hu13H5  VIWRSGSTDYNAAFMS RFTISRDNSKNTLYLQMNSLRAEDTAVYYCAR mu13H5  KAFYVMDY WGQGTSVTVSS
        ********      *
hu13H5  KAFYVMDY WGQGTLVTVSS
```

FIGURE 1B

```
mu13H5  DIQMTQTTSSLSASLGDRVTISC RASQDISIYLN WYQQKPDGTVKLLIY
        *****   *******  ****    **********  *****  ******
hu13H5  DIQMTQSPSSLSASVGDRVTITC RASQDISIYLN WYQQKPGKAPKLLIY mu13H5  YTSRLHS GVPSRFSGSGSGTNFSLTITNLEEEDIATYFC QQGNTLPWT
        *******          *   *  *      * *  *********
hu13H5  YTSRLHS GVPSRFSGSGSGTDFTLTISSLQPEDFATYYC QQGNTLPWT mu13H5  FGGGTKLEIKRT
        *    *******
hu13H5  FGQGTKVEIKRT
```

|  | 100 ----------CDR-H3--------- | 110 | | | | | | | |
|---|---|---|---|---|---|---|---|---|---|
| 70E8 | | W | G | Q | G | T | L | V | T | V | S | A |
| 18B3 | | W | G | Q | G | V | M | V | T | V | S | S |
| 13H5 | | W | G | Q | G | T | S | V | T | V | S | S |
| 49A5 | | W | G | Q | G | T | S | V | T | V | S | S |
| 4G8 | | W | G | A | G | T | T | V | T | V | S | S |
| 54A11 | | W | G | Q | G | T | T | L | T | V | S | S |
| 54C11 | | W | G | Q | G | T | L | V | T | V | S | A |
| 61C11 | | W | G | R | G | T | L | V | T | V | S | A |

FIGURE 2B

```
           1                    10                   20    23
                                                           -------CDRL1-------              30
70E8    D I V M T Q S Q K F M S T S V G D R V S V T C [CDRL1]
18B3    N I Q L T Q S P S S L S A S V G D R V T L S C [CDRL1]
13H5    D I Q M T Q T T S S L S A S L G D R V T I N C [CDRL1]
49A5    D I Q M T Q S Q K F M S T S A S V G D R V S V T C [CDRL1]
4G8     D I V M T Q T Q K F M S T L S V T P G D S V S L S C [CDRL1]
54A11   E I V L T Q S P A T L S V T P G D R V S V T C [CDRL1]
54C11   D I V M T Q S Q K F M S T S V G D R V S V T C [CDRL1]
61C11   D I L L T Q S P A I L S V S P G E R V S F S C [CDRL1]

35                   40                   50
                                           -------CDRL2-------              60
70E8    W Y Q Q I P G H S P K V L I Y           G V P D R F T G S G S G T
18B3    W Y Q Q K L G E A P K L L I H           G I P L R F S G S G S G T
13H5    W Y Q Q K P D G T V K L L I Y           G V P S R F S G S G S G T
49A5    W Y Q Q N P D G S P K L L I Y           G V P D R F T G S G S G T
4G8     W Y Q Q K S G Q S P R L L I Y           E V P S R F S G S G S G T
54A11   W Y H Q R P G E S P R L L I K           G I P S R F S G S G S G T
54C11   W Y Q Q K P D H S P K L L I Y           G V P D R F T G S G S G T
61C11   W Y Q Q R T D H S P R L L I Q           G I P S R F S G S G S G T 70                   80                   90
                                           -------CDRL3-------             100
70E8    D F T L T I S N V Q S E D L A E Y F C [CDRL3] F G G G T K L E I K R T
18B3    D Y T L T I S S L H C E E D D L A T Y Y C [CDRL3] F G G P G T K L E L K R T
13H5    N F S L T I T N L E Q E D D I A T Y F C [CDRL3] F G G G T K L E L K R T
49A5    D Y S L T I H N V Q S E D L A E Y F C [CDRL3] F G G G T K L E I K R T
4G8     D F T L T I H N V E T E D F G M Y F C [CDRL3] F G T G T K L E I V R T
54A11   D F T L T I N N V Q S E D L A E Y F C [CDRL3] F G A G T K L E L K R T
54C11   D F T L T I S N V Q S E D L A E Y F C [CDRL3] F G G G T K L E I R R T
61C11   D F T F T I N S V E S E D I A V Y Y C [CDRL3] F G G G T K L E V K R T
```

FIGURE 3A

Humanized 13H5 heavy chain VH-III

```
             10         20         30         40         50         60
              *          *          *          *          *          *
13H5    QVLLKQSGPSLVQPSQSLSITCTVS GFSLSRYGVH WVRQSPGKGLEWLG VIWRSGSTDYNAAFMS
hu13H5  QVQLVESGGGVVQPGRSLRLSCAAS GFSLSRYGVH WVRQAPGKGLEWVA VIWRSGSTDYNAAFMS
                               V                       LG                  K 70         80         90        100        110
              *          *          *          *          *
13H5    RLSITQDNSKSQVFFMNSLQSDDSAIYYCAK KAFYVMDY WGQGTSVTVSS
hu13H5  RFTISRDNSKNTLYLQMNSLRAEDTAVYYCAR KAFYVMDY WGQGTLVTVSS
         L   Q    S V              K                 S
```

FIGURE 3B

Humanized 13H5 light chain VLK-I

```
             10         20         30         40         50
              *          *          *          *          *
13H5    DIQMTQTTSSLSASLGDRVTISC RASQDISIYLN WYQQKPDGTVKLLIY YTSRLHS
hu13H5  DIQMTQSPSSLSASVGDRVTITC RASQDISIYLN WYQQKPGKAPKLLIY YTSRLHS 60         70         80         90        100
              *          *          *          *          *
13H5    GVPSRFSGSGSGTNFSLTITNLEEEDIATYFC QQGNTLPWT FGGGTKLEIKR
hu13H5  GVPSRFSGSGSGTDFTLTISSLQPEDFATYYC QQGNTLPWT FGQGTKVEIKR
                     N                   Q
```

ENGINEERED ANTI-TSLPR ANTIBODIES

CROSS REFERENCE TO RELATED APPLICATIONS

This application is the national stage application under 35 U.S.C. 371 of International Patent Application No.: PCT/US2009/033383, having an international filing date of Feb. 6, 2009 which claims benefit of U.S. Provisional Application No. 61/026,833, filed Feb. 7, 2008 and U.S. Provisional Application No. 61/042,030, filed on Apr. 3, 2008. Each of the aforementioned PCT and Provisional applications is incorporated by reference in its entirety as if fully set forth herein.

FIELD OF THE INVENTION

The present invention relates generally to a thymic stromal lymphopoietin receptor (TSLPR) specific antibody, and uses thereof, particularly in inflammatory, and allergic inflammatory disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. An immune response can produce pathological consequences, e.g., when it involves excessive inflammation, as in allergic inflammatory disorders.

TSLP is an immune cytokine that induces dendritic cell-mediated CD4$^+$ T cell responses with a proallogenic phenotype (Gilliet et al., *J. Exp. Medicine* 197(8): 1059-1063 (2003). TSLP is involved in the initiation of allergic inflammation (Watanabe et al., *Nature Immunology* 5: 426-434 (2004); Soumelis et al., *Nature Immunology* 3: 673-680 (2002)).

The TSLPR chain is a member of the hematopoietin receptor family and binds to TSLP with low affinity. A combination of TSLPR and IL-7Ralpha chain results in high-affinity binding and in STATS activation and cell proliferation to TSLP stimulation.

Antibodies are being developed against a number of antigen targets that are involved in immune diseases. The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al. (1986) *Nature* 321:522; Verhoeyen et al. (1988) *Science* 239: 1534. However, CDR loop exchanges may not uniformly result in an antibody with the same binding properties as the antibody of origin. Changes in framework residues (FR), residues involved in CDR loop support, in humanized antibodies may also be required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology (NY)* 9:421-5.

The present invention provides an engineered TSLPR antibody and uses thereof to treat inflammatory, and particularly allergic inflammatory, disorders.

SUMMARY OF THE INVENTION

The invention comprises antibodies that bind to the human TSLPR.

In one embodiment, the invention comprises a binding compound that specifically binds human TSLPR, comprising: (i) at least one antibody heavy chain variable region or a TSLPR-binding fragment thereof, said heavy chain variable region comprising at least one CDR sequence selected from the group consisting of SEQ ID NOs: 1, 2, 3, 73, 7, 8, 9, 13, 14, 15, 19, 20, 21, 25, 26, 27, 31, 32, 33, 37, 38, 39, 43, 44 and 45, or a variant of any said sequence; or (ii) at least one antibody light chain variable region or a TSLPR-binding fragment thereof, said light chain variable region comprising at least one CDR sequence selected from the group consisting of SEQ ID NOs: 4, 5, 6, 74, 10, 11, 12, 16, 17, 18, 22, 23, 24, 28, 29, 30, 34, 35, 36, 40, 41, 42, 46, 47 and 48, or a variant of any said sequence.

In another embodiment, the invention comprises a binding compound that specifically binds human TSLPR comprising: (i) at least one antibody heavy chain variable region or a TSLPR-binding fragment thereof, said heavy chain variable region comprising at least one CDR sequence selected from the group consisting of SEQ ID NOs: 1, 2, 3, 73, 7, 8, 9, 13, 14, 15, 19, 20, 21, 25, 26, 27, 31, 32, 33, 37, 38, 39, 43, 44 and 45, or a variant of any said sequence; and (ii) at least one antibody light chain variable region or a TSLPR-binding fragment thereof, said light chain variable region comprising at least one CDR sequence selected from the group consisting of SEQ ID NOs: 4, 5, 6, 74, 10, 11, 12, 16, 17, 18, 22, 23, 24, 28, 29, 30, 34, 35, 36, 40, 41, 42, 46, 47 and 48, or a variant of any said sequence.

In another embodiment, the invention comprises a binding compound that specifically binds human TSLPR comprising: (i) at least one antibody heavy chain variable region or a TSLPR-binding fragment thereof, said heavy chain variable region comprising at least two CDR sequence selected from the group consisting of SEQ ID NOs: 1, 2, 3, 73, 7, 8, 9, 13, 14, 15, 19, 20, 21, 25, 26, 27, 31, 32, 33, 37, 38, 39, 43, 44 and 45, or a variant of any said sequence; and (ii) at least one antibody light chain variable region or a TSLPR-binding fragment thereof, said light chain variable region comprising at least two CDR sequence selected from the group consisting of SEQ ID NOs: 4, 5, 6, 74, 10, 11, 12, 16, 17, 18, 22, 23, 24, 28, 29, 30, 34, 35, 36, 40, 41, 42, 46, 47 and 48, or a variant of any said sequence.

In another embodiment, the invention comprises a binding compound that specifically binds human TSLPR comprising: (i) at least one antibody heavy chain variable region or a TSLPR-binding fragment thereof, said heavy chain variable region comprising at least three CDR sequence selected from the group consisting of SEQ ID NOs: 1, 2, 3, 73, 7, 8, 9, 13, 14, 15, 19, 20, 21, 25, 26, 27, 31, 32, 33, 37, 38, 39, 43, 44 and 45, or a variant of any said sequence; and (ii) at least one antibody light chain variable region or a TSLPR-binding fragment thereof, said light chain variable region comprising at least three CDR sequence selected from the group consisting of SEQ ID NOs: 4, 5, 6, 74, 10, 11, 12, 16, 17, 18, 22, 23, 24, 28, 29, 30, 34, 35, 36, 40, 41, 42, 46, 47 and 48, or a variant of any said sequence.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 1, 2, and 3, or variants of any said sequences; and (ii) at least one antibody light chain variable region of a TSLPR-binding fragment thereof, said light chain variable region comprising the three CDR sequences set forth in SEQ ID NOs: 4, 5, and 6, or variants of any said sequences.

In another embodiment, the invention comprises a binding compound that specifically binds human TSLPR comprising: the CDR-H1 sequence of SEQ ID NO:1 or a variant thereof, the CDR-H2 sequence of SEQ ID NO:2 of a variant thereof, and the CDR-H3 sequence of SEQ ID NO:3 or SEQ ID NO:73 or a variant of thereof; and the CDR-L1 sequence of SEQ ID NO:4 or a variant of thereof, the CDR-L2 sequence of SEQ ID NO:5 or a variant of thereof, and the CDR-L3 sequence of SEQ ID NO:6 or SEQ ID NO:74 or a variant of thereof.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 7, 8 and 9, or variants of any said sequences; and (ii) at least one antibody light chain variable region of a TSLPR-binding fragment thereof, said light chain variable region comprising the three CDR sequences set forth in SEQ ID NOs: 10, 11 and 12, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 13, 14 and 15, or variants of any said sequences; and (ii) at least one antibody light chain variable region of a TSLPR-binding fragment thereof, said light chain variable region comprising the three CDR sequences set forth in SEQ ID NOs: 16, 17 and 18, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 19, 20 and 21, or variants of any said sequences; and (ii) at least one antibody light chain variable region of a TSLPR-binding fragment thereof, said light chain variable region comprising the three CDR sequences set forth in SEQ ID NOs: 22, 23 and 24, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 25, 26 and 27, or variants of any said sequences; and (ii) at least one antibody light chain variable region of a TSLPR-binding fragment thereof, said light chain variable region comprising the three CDR sequences set forth in SEQ ID NOs: 28, 29 and 30, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 31, 32 and 33, or variants of any said sequences; and (ii) at least one antibody light chain variable region of a TSLPR-binding fragment thereof, said light chain variable region comprising the three CDR sequences set forth in SEQ ID NOs: 34, 35 and 36, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 37, 38 and 399, or variants of any said sequences; and (ii) at least one antibody light chain variable region of a TSLPR-binding fragment thereof, said light chain variable region comprising the three CDR sequences set forth in SEQ ID NOs: 40, 41 and 42, or variants of any said sequences.

In another embodiment, the invention comprises a binding compound that specifically binds human TSLPR comprising: (i) at least one antibody heavy chain variable region or a TSLPR-binding fragment thereof, said heavy chain variable region comprising the three CDR sequences set forth in SEQ ID NOs: 43, 44 and 45, or variants of any said sequences; and (ii) at least one antibody light chain variable region of a TSLPR-binding fragment thereof, said light chain variable region comprising the three CDR sequences set forth in SEQ ID NOs: 46, 47 and 48, or variants of any said sequences.

In one embodiment, the invention comprises a binding compound comprising a heavy chain variable region comprising residues 1-116 of SEQ ID NO: 51 or a variant of said sequence; and a light chain variable region comprising residues 1-108 of SEQ ID NO: 52 or a variant of said sequence.

In one embodiment, the invention comprises a binding compound comprising a heavy chain variable region comprising residues 1-116 of SEQ ID NO: 57 or a variant of said sequence; and a light chain variable region comprising residues 1-108 of SEQ ID NO: 58 or a variant of said sequence.

In one embodiment, the invention comprises a binding compound comprising a heavy chain variable region comprising residues 1-116 of SEQ ID NO: 61 or a variant of said sequence; and a light chain variable region comprising residues 1-108 of SEQ ID NO: 62 or a variant of said sequence.

In any of the above embodiments, the variant may comprise up to three conservatively modified amino acid residues. In a one embodiment, the variant may comprise three conservatively modified amino acid residues. In another embodiment, the variant may comprise two conservatively modified amino acid residues. In yet another embodiment, the variant may comprise one conservatively modified amino acid residue.

In one embodiment, the invention comprises a binding compound that specifically binds human TSLP, comprising:

(i) a heavy chain variable region having at least 90% homology to an amino acid sequence selected from the group consisting of: 51, 57 and 61; and (ii) a light chain variable region having at least 90% homology to an amino acid sequence selected from the group consisting of 52, 58 and 62.

In some embodiments, the above described binding compounds block the binding of TSLP to TSLPR and/or block TSLPR-mediated activity.

In any of the above described embodiments, the binding compound is an antibody or an antibody fragment.

In any of the above described embodiments, the binding compound may be a humanized antibody or a TSLPR-binding fragment thereof.

In one embodiment, the binding compound is a TSLPR-binding antibody fragment selected from the group consisting of Fab, Fab', Fab'-SH, Fv, scFv, F(ab')$_2$, and a diabody.

In any of the above described embodiment, the binding compound may further comprise a human heavy chain constant region or a variant thereof, wherein the variant comprises up to 20 conservatively modified amino acid substitutions; or a human light chain constant region or a variant thereof, wherein the variant comprises up to 20 conservatively modified amino acid substitutions.

In any of the above described embodiment, the binding compound may further comprise a γ4 or γ1 human heavy chain constant region or a variant thereof, wherein the variant comprises up to 20 conservatively modified amino acid substitutions.

In a preferred embodiment, the human variable heavy domain will be grafted onto an IgG4 backbone to eliminate effector function.

The invention also comprises an antibody or antigen binding fragment thereof that specifically binds to the epitope on human TSLPR that is bound by an antibody selected from the group consisting of antibodies 13H5, 70E8, 54C11, 49A5, 4G8, 54A11, 61C11 and 18B3.

The invention further comprises an antibody or antigen binding fragment thereof that competitively inhibits binding by an antibody selected from the group consisting of antibodies 13H5, 70E8, 54C11, 49A5, 4G8, 54A11, 61C11 and 18B3.

The invention also comprises isolated nucleic acids encoding the binding compounds of the invention. The invention also comprises expression vectors comprising the above described nucleic acids. In one embodiment, the expression vector is operably linked to control sequences that are recognized by a host cell when the host cell is transfected with the vector. The invention also comprises a method of producing a polypeptide comprising: culturing the above described host cells in culture medium under conditions wherein the nucleic acid sequence is expressed, thereby producing polypeptides comprising the light and heavy chain variable regions; and recovering the polypeptides from the host cell or culture medium.

The invention also comprises a method of suppressing an immune response in a human subject comprising administering to a subject in need thereof any one of the above described binding compounds or a TSLPR-binding fragment thereof, in an amount effective to block the biological activity of TSLPR. In one embodiment, the immune response is an inflammatory response. In one embodiment, the subject has a disorder selected from the group consisting of allergic rhinosinusitis, allergic asthma, allergic conjunctivitis, or atopic dermatitis. In a preferred embodiment, the subject has asthma.

The invention also comprises a composition comprising any of the above described binding compounds in combination with a pharmaceutically acceptable carrier or diluent.

The invention also comprises the use of any of the binding compounds of the invention for the preparation of a medicament to suppress an immune response.

The invention also comprises the use of any of the binding compounds of the invention for the preparation of a medicament to treat inflammation.

The invention also comprises the use of any of the binding compounds of the invention for the preparation of to treat allergic inflammation.

The invention also comprises the use of any of the binding compounds of the invention for the preparation of a medicament to treat allergic rhinosinusitis, allergic asthma, allergic conjunctivitis, or atopic dermatitis.

The invention also comprises the use of any of the binding compounds of the invention for the preparation of a medicament to treat asthma.

BRIEF DESCRIPTION OF THE DRAWINGS

FIG. 1A is an alignment of the variable domains of the heavy chain of the murine and humanized 13H5 antibodies (SEQ ID NOs: 49 and 51, respectively). The differences between the murine and humanized antibodies are indicated with an asterisk. The CDR sequences are in bold.

FIG. 1B is an alignment of the variable domains of the light chain of the murine and humanized 13H5 antibodies (SEQ ID NOs: 50 and 52, respectively). The differences between the murine and humanized antibodies are indicated with an asterisk. The CDR sequences are in bold.

Figure 2A:
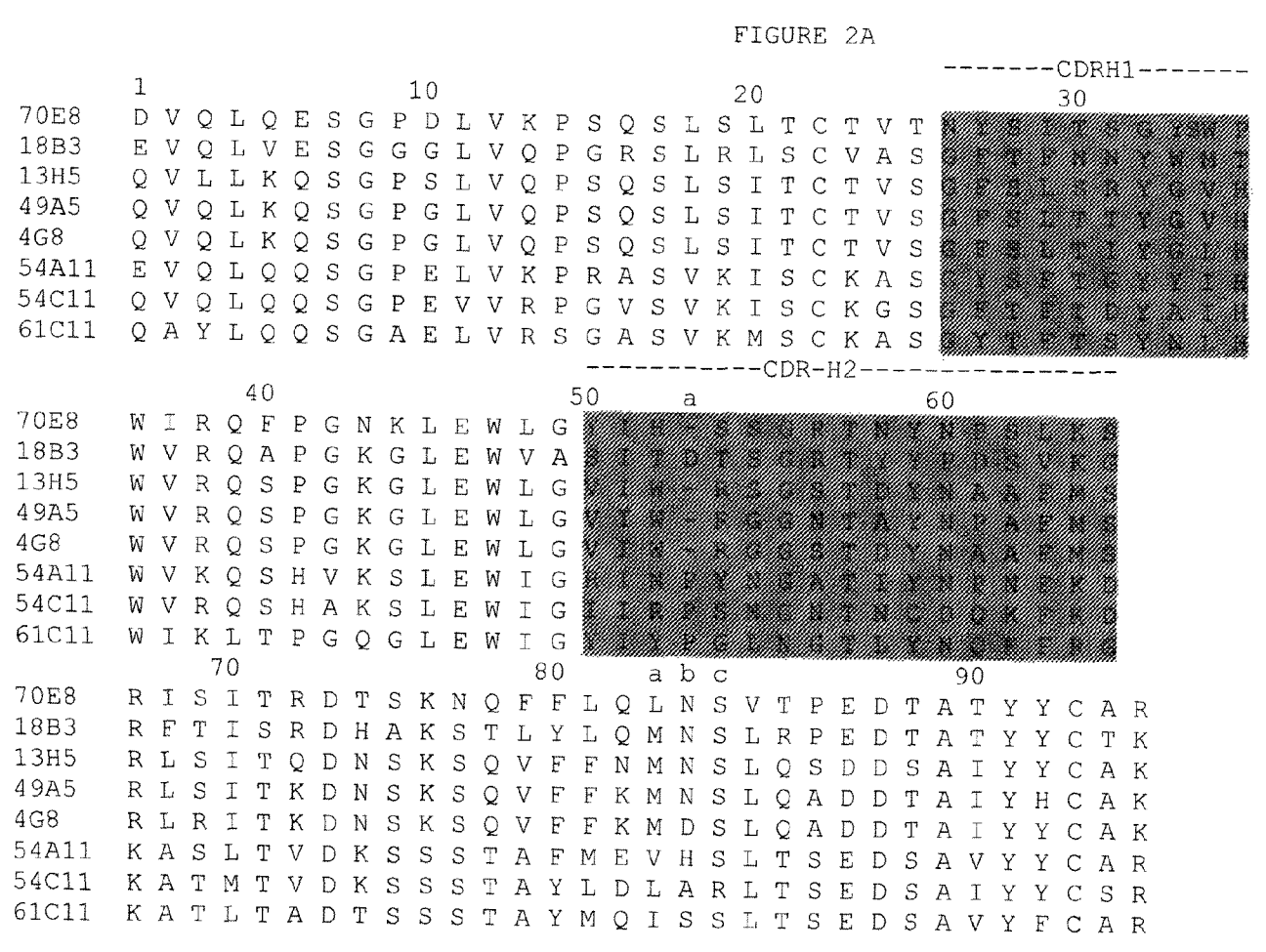

FIG. 2A is an alignment of the variable domains of the heavy chain of the rat antibody 18B3 (SEQ ID NO:71) and mouse antibodies 70E8 (SEQ ID NO:55), 13H5 (SEQ ID NO:49), 49A5 (SEQ ID NO:63), 4G8 (SEQ ID NO:65), 54A11 (SEQ ID NO:67), 54C11 (SEQ ID NO:59) and 61C11 (SEQ ID NO:69). The CDR sequences are highlighted.

FIG. 2B is an alignment of the variable domains of the light chain of the rat antibody 18B3 (SEQ ID NO:72) and mouse antibodies 70E8 (SEQ ID NO:56), 13H5 (SEQ ID NO:50), 49A5 (SEQ ID NO:64), 4G8 (SEQ ID NO:66), 54A11 (SEQ ID NO:68), 54C11 (SEQ ID NO:60) and 61C11 (SEQ ID NO:70). The CDR sequences are highlighted.

FIG. 3A illustrates possible variable domain sequences for the heavy chain of hu13H5 (SEQ ID NO:53).

FIG. 3B illustrates possible variable domain sequences for the light chain of hu13H5 (SEQ ID NO:54).

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. DEFINITIONS

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation"

can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications.

As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, the term "TSLPR binding fragment" or "binding fragment thereof" encompasses a fragment or a derivative of an antibody that still substantially retain its biological activity of inhibiting TSLPR activity. Therefore, the term "antibody fragment" or TSLPR binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; domain antibodies; and multispecific antibodies formed from antibody fragments. Typically, a binding fragment or derivative retains at least 10% of its TSLPR inhibitory activity. Preferably, a binding fragment or derivative retains at least 25%, 50%, 60%, 70%, 80%, 90%, 95%, 99% or 100% (or more) of its TSLPR inhibitory activity, although any binding fragment with sufficient affinity to exert the desired biological effect will be useful. It is also intended that a TSLPR binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al., (1991) *Nature* 352: 624-628 and Marks et al., (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad Sci. USA* 81: 6851-6855).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hu" or "hum" is added to antibody clone designations when necessary to distinguish humanized antibodies (e.g., "hu13H5") from parental rodent antibodies (e.g., mouse 13H5, or "m13H5"). The humanized forms of rodent antibodies will generally comprise the same CDR sequences of the parental rodent antibodies, although certain amino acid substitutions may be included to increase affinity or increase stability of the humanized antibody.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. See Tables 2 and 3, in which sequence numbering is with reference to the Sequence Listing.

"Binding" refers to an association of the binding composition with a target where the association results in reduction in the normal Brownian motion of the binding composition, in cases where the binding composition can be dissolved or suspended in solution.

"Binding compound" refers to a molecule that comprises one or more amino acid sequences that specifically bind to human TSLPR. In one preferred embodiment, the binding compound is an antibody. In another preferred embodiment, the binding compound comprises an antibody fragment.

"Binding composition" refers to a TSLPR-binding compound in combination with a stabilizer, excipient, salt, buffer, solvent, or additive, capable of binding to a target.

"Conservatively modified variants" or "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth in Table 1 as follows:

TABLE 1

Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The terms "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a nonlimiting example, an antibody or fragment thereof that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888, 530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context.

"Endogenous" refers to substances that are produced within a cell, organism, or human body, depending on the context.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin DNA may be used.

"Inhibitors" are compounds that decrease, block, prevent, delay activation, inactivate, desensitize, or down regulate, e.g., a gene, protein, ligand, receptor, or cell. An inhibitor may also be defined as a composition that reduces, blocks, or inactivates a constitutive activity. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%.

Endpoints in inhibition can be monitored as follows. Inhibition, and response to treatment, e.g., of a cell, physiological fluid, tissue, organ, and animal or human subject, can be monitored by an endpoint. The endpoint may comprise a predetermined quantity or percentage of. e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Specifically" or "selectively" binds, when referring to a ligand/receptor, antibody/antigen, or other binding pair, indicates a binding reaction which is determinative of the presence of the protein, e.g., TSLPR, in a heterogeneous population of proteins and/or other biologics. Thus, under designated conditions, a specified ligand/antigen binds to a particular receptor/antibody and does not bind in a significant amount to other proteins present in the sample.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis (Munsen, et al. (1980) *Analyt. Biochem.* 107:220-239).

As used herein, the term "inflammatory disorder" refers to any disease or disorder characterized by local inflammation at a site of injury or infection and includes, without limitation, allergic inflammation, autoimmune diseases, and other disorders characterized by undesired immune cell accumulation at a local tissue site.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherpeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

II. GENERAL

The present invention provides engineered anti-TSLPR antibodies and uses thereof to treat inflammatory, and particularly allergic inflammatory, disorders. In a preferred embodiment, the inflammatory disorder is asthma. In a preferred embodiment, the allergic inflammatory disorder is allergic rhinosinusitis, allergic asthma, allergic conjunctivitis, or atopic dermatitis. The present invention also provides engineered anti-TSLPR antibodies to treat fibrosis, inflammatory bowel disease or Hodgkin's lymphoma.

TSLP is a member of the 'long chain' family of hematopoetic cytokines. Insights into the structural basis of 'long chain' cytokine/receptor recognition have shown that although large areas of protein surface are buried in formation of cytokine-receptor complexes, the affinity of the interaction is dominated by a few, often tightly clustered amino acid residues forming an energetic 'hot spot' in the center of the binding interface. The identity of the residues that dominate the binding energy of a large protein-protein interface has been termed the 'functional epitope'. The affinity of the interaction (and hence biological specificity) is consequently defined by the structural complementarity of the functional epitopes of ligand and receptor. Detailed mutagenesis studies have shown that the most significant residues that make up the functional epitopes of cytokines and receptors are hydrophobic contacts involving either non-polar side chains such as tryptophan, the aliphatic components of non-polar side chains or the polypeptide backbone. The non-polar 'core' is surrounded by a halo of polar residues of lesser importance for binding energy. Kinetic studies indicate that the primary role of the functional epitopes is to stabilize protein-protein interaction by decreasing the dissociation rate of the complex. It has been suggested that the initial contact between cytokine and receptor is dominated by random diffusion or 'rolling' of protein surfaces producing many unstable contacts. The complex is then stabilized when the functional epitopes of the receptor and ligand engage (see, e.g., Bravo and Heath, supra).

III. GENERATION OF TSLPR SPECIFIC ANTIBODIES

Any suitable method for generating monoclonal antibodies may be used. For example, a recipient may be immunized with TSLPR, or a fragment thereof. Any suitable method of immunization can be used. Such methods can include adjuvants, other immunostimulants, repeated booster immunizations, and the use of one or more immunization routes.

Any suitable source of TSLPR can be used as the immunogen for the generation of the non-human antibody, of the compositions and methods disclosed herein. Such forms include, but are not limited to whole protein, including linked and naturally occurring heterodimers, peptide(s), and epitopes, generated through recombinant, synthetic, chemical or enzymatic degradation means known in the art.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit TSLPR. It is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle, et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275-1281.

Other suitable techniques involve selection of libraries of antibodies in phage or similar vectors. See, e.g., Huse et al., *Science* 246:1275-1281 (1989); and Ward et al., *Nature* 341: 544-546 (1989). The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci. USA* 86:10029-10033; or made in transgenic mice, see Mendez et al. (1997) *Nature Genetics* 15:146-156; also see Abgenix and Medarex technologies.

Antibodies or binding compositions against predetermined fragments of TSLPR can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective TSLPR. These monoclonal antibodies will usually bind with at least a $K_d$ of about 1 µM, more usually at least about 300 nM, typically at least about 30 nM, preferably at least about 10 nM, more preferably at least about 3 nM or better, usually determined by ELISA.

IV. HUMANIZATION OF TSLPR SPECIFIC ANTIBODIES

Any suitable non-human antibody can be used as a source for the hypervariable region. Sources for non-human antibodies include, but are not limited to, murine, Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance of the desired biological activity. For further details, see Jones et al. (1986) *Nature* 321:522-525; Reichmann et al. (1988) *Nature* 332:323-329; and Presta (1992) *Curr. Op. Struct. Biol.* 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239400).

Amino acid sequence variants of humanized anti-TSLPR antibody are prepared by introducing appropriate nucleotide changes into the humanized anti-TSLPR antibody DNA, or by peptide synthesis. Such variants include, for example, deletions from, and/or insertions into and/or substitutions of, residues within the amino acid sequences shown for the humanized anti-TSLPR F(ab). Any combination of deletion, insertion, and substitution is made to arrive at the final construct, provided that the final construct possesses the desired characteristics. The amino acid changes also may alter post-translational processes of the humanized anti-TSLPR antibody, such as changing the number or position of glycosylation sites.

A useful method for identification of certain residues or regions of the humanized anti-TSLPR antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with TSLPR antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-TSLPR antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-TSLPR antibody with an N-terminal methionyl residue or the antibody fused to an epitope tag. Other insertional variants of the humanized anti-TSLPR antibody molecule include the fusion to the N- or C-terminus of humanized anti-TSLPR antibody of an enzyme or a polypeptide which increases the serum half-life of the antibody.

Another type of variant is an amino acid substitution variant. These variants have at least one amino acid residue in the humanized anti-TSLPR antibody molecule removed and a different residue inserted in its place. The sites of greatest interest for substitutional mutagenesis include the hypervariable loops, but FR alterations are also contemplated. Hypervariable region residues or FR residues involved in antigen binding are generally substituted in a relatively conservative manner.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. In one embodiment, the asparagine is changed to glutamine (Q). Isoaspartate formation may debilitate or completely abrogate binding of an antibody to its target antigen. Presta (2005) *J. Allergy Clin. Immunol.* 116:731 at 734. In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease TSLPR binding affinity to unacceptable levels.

Nucleic acid molecules encoding amino acid sequence variants of humanized TSLPR specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-TSLPR antibody.

Ordinarily, amino acid sequence variants of the humanized anti-TSLPR antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%. Identity or homology with respect to this sequence is defined herein as the percentage of amino acid residues in the candidate sequence that are identical with the humanized anti-TSLPR residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

CDR and FR residues are determined according to the standard sequence definition of Kabat. Kabat et al., Sequences of Proteins of Immunological Interest, National Institutes of Health, Bethesda Md. (1987).

Table 2 provides sequence identifier information for the certain mouse and human variable heavy chain CDRs. Table 3 provides sequence identifier information for certain mouse and human variable light chain CDRs.

TABLE 2

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDR-H1 | CDR-H2 | CDR-H3 |
| m13H5 | 49 | 1-116 | 26-35 | 50-65 | 98-105 |
| hu13H5 | 51 | 1-116 | 26-35 | 50-65 | 98-105 |
| m70E8 | 55 | 1-119 | 26-36 | 51-66 | 99-108 |
| h70E8 | 57 | 1-119 | 26-36 | 51-66 | 99-108 |
| m54C11 | 59 | 1-119 | 26-35 | 50-66 | 99-108 |
| h54C11 | 61 | 1-119 | 26-35 | 50-66 | 99-108 |
| m49A5 | 63 | 1-119 | 26-35 | 50-65 | 98-108 |
| m4G8 | 65 | 1-121 | 26-35 | 50-65 | 98-110 |
| m54A11 | 67 | 1-119 | 26-35 | 50-66 | 99-108 |
| m61C11 | 69 | 1-119 | 26-35 | 50-66 | 99-108 |
| r18B3 | 71 | 1-117 | 26-35 | 50-66 | 99-106 |

TABLE 3

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDR-L1 | CDR-L2 | CDR-L3 |
| m13H5 | 50 | 1-108 | 24-34 | 50-56 | 89-97 |
| hu13H5 | 52 | 1-108 | 24-34 | 50-56 | 89-97 |
| m70E8 | 56 | 1-108 | 24-34 | 50-56 | 89-97 |
| h70E8 | 58 | 1-108 | 24-34 | 50-56 | 89-97 |
| m54C11 | 60 | 1-108 | 24-34 | 50-56 | 89-97 |
| h54C11 | 62 | 1-108 | 24-34 | 50-56 | 89-97 |
| m49A5 | 64 | 1-108 | 25-34 | 50-56 | 89-97 |
| m4G8 | 66 | 1-108 | 25-34 | 50-56 | 89-97 |
| m54A11 | 68 | 1-107 | 25-34 | 50-56 | 89-96 |
| m61C11 | 70 | 1-108 | 25-34 | 50-56 | 89-97 |
| r18B3 | 72 | 1-107 | 25-34 | 50-56 | 89-96 |

The m13H5 and hu13H5CDR-H1 sequence is GFSLSRYGVH (SEQ ID NO. 1). The m13H5 and hu13H5CDR-H2 sequence is VIWRSGSTDYNAAFMS (SEQ ID NO. 2). The m13H5 and hu13H5CDR-H3 sequence is KAFYVMDY (SEQ ID NO. 3). An alternative sequence for hu13H5CDR-H2 is VIWRSGSTDYNAAFKS (SEQ ID NO. 73).

The m13H5 and hu13H5CDR-L1 sequence is RASQDISIYLN (SEQ ID NO. 4). The m13H5 and hu13H5CDR-L2 sequence is YTSRLHS (SEQ ID NO. 5). The m13H5 and hu13H5CDR-L3 sequence is QQGNTLPWT (SEQ ID NO. 6). An alternative sequence for hu13H5CDR-L3 is QQGQTLPWT (SEQ ID NO. 74).

The m13H5 variable heavy chain amino acid sequence is set forth in SEQ ID NO: 49.

The m13H5 variable light chain amino acid sequence is set forth in SEQ ID NO: 50.

The hu13H5 variable heavy chain amino acid sequence is set forth in SEQ ID NO: 51.

The hu13H5 variable light chain amino acid sequence is set forth in SEQ ID NO: 52.

Alternative sequences for the variable heavy chain of hu13H5 can be found in SEQ ID NO: 53 (FIG. 3A). The amino acid at position 24 could be A or V. The amino acid at position 48 could be V or L. The amino acid at position 49 could be A or G. The amino acid at position 64 could be M or K. The amino acid at position 67 could be F or L. The amino acid at position 71 could be R or Q. The amino acid at position 76 could be N or S. The amino acid at position 78 could be L or V. The amino acid at position 97 could be R or K. The amino acid at position 111 could be L or S. (The potential change at amino acid position 64 may alleviate potential problems with Asn deamidation ormethionine oxidation.)

Alternative sequences for the variable light chain of hu13H5 can be found in SEQ ID NO: 54 (FIG. 3B). The amino acid at position 70 could be D or N. The amino acid at position 92 could be N or Q. The potential change at position 70 could introuce an N-linked gluycosylation site into the humanized antibody that is present in the murine antibody.

The m70E8 and hu70E8 CDR-H1 sequence is NYSITSGYSWP (SEQ ID NO. 7). The m70E8 and hu70E8 CDR-H2 sequence is YIHSSGRTNYNPSLKS (SEQ ID NO. 8). The m70E8 and hu70E8 CDR-H3 sequence is SQLGLVFFAY (SEQ ID NO. 9).

The m70E8 and hu70E8 CDR-L1 sequence is KASQSVGANVA (SEQ ID NO. 10). The m70E8 and hu70E8 CDR-L2 sequence is SASYRFS (SEQ ID NO. 11). The m70E8 and hu70E8 CDR-L3 sequence is QQYNSYPYT (SEQ ID NO. 12).

The m70E8 variable heavy chain amino acid sequence is set forth in SEQ ID NO: 55.

The m70E8 variable light chain amino acid sequence is set forth in SEQ ID NO: 56.

The hu70E8 heavy chain amino acid sequence is set forth in SEQ ID NO: 57.

The hu70E8 light chain amino acid sequence is set forth in SEQ ID NO: 58.

The m54C11 and hu54C11 CDR-H1 sequence is GFTFTDYAIH (SEQ ID NO. 13). The m54C11 and hu54C11 CDR-H2 sequence is IIRPSNGNTNCDQKFKD (SEQ ID NO. 14). The m54C11 and hu54C11 CDR-H3 sequence is SRVWGGSLAY (SEQ ID NO. 15).

The m54C11 and hu54C11 CDR-L1 sequence is KASQNVGTNIA (SEQ ID NO. 16). The m54C11 and hu54C11 CDR-L2 sequence is SASYRYS (SEQ ID NO. 17). The m54C11 and hu54C11 CDR-L3 sequence is QQYKSYPWT (SEQ ID NO. 18).

The m54C11 variable heavy chain amino acid sequence is set forth in SEQ ID NO: 59.

The m54C11 variable light chain amino acid sequence is set forth in SEQ ID NO: 60.

The hu54C11 heavy chain amino acid sequence is set forth in SEQ ID NO: 61.

The hu54C11 light chain amino acid sequence is set forth in SEQ ID NO: 62.

The m49A5 CDR-H1 sequence is GFSLTTYGVH (SEQ ID NO. 19). The m49A5 CDR-H2 sequence is VIWRGGN-TAYNPAFMS (SEQ ID NO. 20). The m49A5 CDR-H3 sequence is KSYYGYHAMGY (SEQ ID NO. 21).

The m49A5 CDR-L1 sequence is ASQDISNYLN (SEQ ID NO. 22). The m49A5 CDR-L2 sequence is YTSRLHS (SEQ ID NO. 23). The m49A5 CDR-L3 sequence is QQANTLPWT (SEQ ID NO. 24).

The m49A5 variable heavy chain amino acid sequence is set forth in SEQ ID NO: 63.

The m49A5 variable light chain amino acid sequence is set forth in SEQ ID NO: 64.

The m4G8 CDR-H1 sequence is GFSLTIYGLH (SEQ ID NO. 25). The m4G8 CDR-H2 sequence is VIWRGGSTDY-NAAFMS (SEQ ID NO. 26). The m4G8 CDR-H3 sequence is PYYDYDGNWYFDV (SEQ ID NO. 27).

The m4G8 CDR-L1 sequence is ASQNVGTNVA (SEQ ID NO. 28). The m4G8 CDR-L2 sequence is SASSHCS (SEQ ID NO. 29). The m4G8 CDR-L3 sequence is QQYNRYPLT (SEQ ID NO. 30).

The m4G8 variable heavy chain amino acid sequence is set forth in SEQ ID NO: 65.

The m4G8 variable light chain amino acid sequence is set forth in SEQ ID NO: 66.

The m54A11 CDR-H1 sequence is GYSFTGYYIH (SEQ ID NO. 31). The m54A11 CDR-H2 sequence is RINPYN-GATIYNPNFKD (SEQ ID NO. 32). The m54A11 CDR-H3 sequence is SYGYVNYFDY (SEQ ID NO. 33).

The m5A411 CDR-L1 sequence is ASQSISNNLH (SEQ ID NO. 34). The m54A11 CDR-L2 sequence is FGFQSIS (SEQ ID NO. 35). The m54A11 CDR-L3 sequence is QQT-NSWLT (SEQ ID NO. 36).

The m54A11 variable heavy chain amino acid sequence is set forth in SEQ ID NO: 67.

The m54A11 variable light chain amino acid sequence is set forth in SEQ ID NO: 68.

The m61C11 CDR-H1 sequence is GYTFTSYNLH (SEQ ID NO. 37). The m61C11 CDR-H2 sequence is YIYPGLNGTLYNQKFRG (SEQ ID NO. 38). The m61C11 CDR-H3 sequence is SDYGKAWFAY (SEQ ID NO. 39).

The m61C11 CDR-L1 sequence is ASQSIATKIH (SEQ ID NO. 40). The m61C11 CDR-L2 sequence is LGSESIS (SEQ ID NO. 41). The m61C11 CDR-L3 sequence is QQSNRY-PYT (SEQ ID NO. 42).

The m61C11 variable heavy chain amino acid sequence is set forth in SEQ ID NO: 69.

The m61C11 variable light chain amino acid sequence is set forth in SEQ ID NO: 70.

The r18B3 CDR-H1 sequence is GFTFNNYWMT (SEQ ID NO. 43). The r18B3CDR-H2 sequence is SITDTSGR-TYYPDSVKG (SEQ ID NO. 44). The r18B3CDR-H3 sequence is TLGGIPRD (SEQ ID NO. 45).

The r18B3 CDR-L1 sequence is GSQNINNYLA (SEQ ID NO. 46). The r18B3CDR-L2 sequence is KTNILQT (SEQ ID NO. 47). The r18B3CDR-L3 sequence is YQFNNGFT (SEQ ID NO. 48).

The r18B3 variable heavy chain amino acid sequence is set forth in SEQ ID NO: 71.

The r18B3 variable light chain amino acid sequence is set forth in SEQ ID NO: 72.

Also contemplated are chimeric antibodies. As noted above, typical chimeric antibodies comprise a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA 81: 6851-6855).

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan, et al. (1985) Science 229: 81. Bispecific antibodies include bispecific antibody fragments. See, e.g., Hollinger, et al. (1993) Proc. Natl. Acad. Sci. U.S.A. 90: 6444-48, Gruber, et al., J. Immunol. 152: 5368 (1994).

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. BIOLOGICAL ACTIVITY OF HUMANIZED ANTI-TSLPR

Antibodies having the characteristics identified herein as being desirable in a humanized anti-TSLPR antibody can be screened for inhibitory biologic activity in vitro or for suitable binding affinity. To screen for antibodies that bind to the epitope on human TSLPR bound by an antibody of interest (e.g., those which block binding of the cytokine to its receptor), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bound at nearby, or even overlapping, epitopes.

Alternatively, epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in human TSLPR may also be used to determine the functional epitope for an anti-TSLPR antibody of the present invention. Mutagenesis studies, however, may also reveal amino acid residues that are crucial to the overall three-dimensional structure of TSLPR but that are not directly involved in antibody-antigen contacts, and thus other methods may be necessary to confirm a functional epitope determined using this method.

The epitope bound by a specific antibody may also be determined by assessing binding of the antibody to peptides comprising fragments of human TSLPR. The amino acid sequence of human TSLPR is set forth in SEQ ID NO: 2 of U.S. Pat. No. 6,982,320 (GenBank Accession No. ABE16323.1; see also GenBank Accession No. NP_071431). A series of overlapping peptides encompassing the sequence of TSLPR may be synthesized and screened for binding, e.g. in a direct ELISA, a competitive ELISA (where the peptide is assessed for its ability to prevent binding of an antibody to TSLPR bound to a well of a microtiter plate), or on a chip. Such peptide screening methods may not be capable of detecting some discontinuous functional epitopes, i.e. functional epitopes that involve amino acid residues that are not contiguous along the primary sequence of the TSLPR polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in TSLPR when free and when bound in a complex with an antibody of interest (Zinn-Justin et al. (1992) *Biochemistry* 31, 11335-11347; Zinn-Justin et al. (1993) *Biochemistry* 32, 6884-6891).

With regard to X-ray crystallography, crystallization may be accomplished using any of the known methods in the art (e.g. Giege et al. (1994) *Acta Crystallogr.* D50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al., eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323), the disclosures of which are hereby incorporated by reference in their entireties.

Additional antibodies binding to the same epitope as an antibody of the present invention may be obtained, for example, by screening of antibodies raised against TSLPR for binding to the epitope, or by immunization of an animal with a peptide comprising a fragment of human TSLPR comprising the epitope sequence. Antibodies that bind to the same functional epitope might be expected to exhibit similar biological activities, such as blocking receptor/ligand binding, and such activities can be confirmed by functional assays of the antibodies.

Antibody affinities (e.g. for human TSLPR) may be determined using standard analysis. Preferred humanized antibodies are those which bind human TSLPR with a $K_D$ value of no more than about $1 \times 10^{-7}$; preferably no more than about $1 \times 10^{-8}$; more preferably no more than about $1 \times 10^{-9}$; and most preferably no more than about $1 \times 10^{-10}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of TSLPR to bind its ligand. In one embodiment, the antibody and fragments thereof useful in the present compositions and methods inhibit: hTSLP induced proliferation of a Baf-3 cell line transfected with hTSLP-receptor and IL-7Ralpha; hTSLP induced luciferase expression from a Baf-3 cell line transfected with the TSLP-receptor and a luciferase reporter system; hTSLP induced TARC secretion from human primary monocytes isolated from PBMCs; and induction of Th2 differentiation.

As used herein, the term "specific" refers to the selective binding of the antibody to the target antigen epitope. Antibodies can be tested for specificity of binding by comparing binding to TSLPR to binding to irrelevant antigen or antigen mixture under a given set of conditions. If the antibody binds to TSLPR at least 10, and preferably 50 times more than to irrelevant antigen or antigen mixture then it is considered to be specific. An antibody that "specifically binds" to TSLPR does not bind to proteins that do not comprise the TSLPR-derived sequences, i.e. "specificity" as used herein relates to TSLPR specificity, and not any other sequences that may be present in the protein in question. For example, as used herein, an antibody that "specifically binds" to TSLPR will typically bind to FLAG-h TSLPR, which is a fusion protein comprising TSLPR and a FLAG® peptide tag, but it does not bind to the FLAG® peptide tag alone or when it is fused to a protein other than TSLPR.

VI. PHARMACEUTICAL COMPOSITIONS

To prepare pharmaceutical or sterile compositions, the antibody or fragment thereof is admixed with a pharmaceutically acceptable carrier or excipient, see, e.g., *Remington's Pharmaceutical Sciences* and *U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tab-

*lets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Antibodies exhibiting high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348: 601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent.

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 μg/kg body weight, more generally at least 0.2 μg/kg, most generally at least 0.5 μg/kg, typically at least 1 μg/kg, more typically at least 10 μg/kg, most typically at least 100 μg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an inflammatory disease.

As used herein, the term "therapeutically effective amount" or "effective amount" refers to an amount of an anti-TSLPR antibody or fragment thereof, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, steroid, chemotherapeutic agent, antibiotic, or radiation, are well known in the art, see, e.g., Hardman, et al. (eds.) (2001) *Goodman and Gilman's The Pharmacological Basis of Therapeutics*, 10th ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA. The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

Typical veterinary, experimental, or research subjects include monkeys, dogs, cats, rats, mice, rabbits, guinea pigs, horses, and humans

VII. ANTIBODY PRODUCTION

For recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-TSLPR antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of the anti-TSLPR antibody are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for TSLPR) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. USES

The present invention provides methods for using engineered anti-TSLPR for the treatment and diagnosis of inflammatory disorders.

In a preferred embodiment, the inflammatory disorder is asthma.

In another preferred embodiment, the inflammatory disorder is an allergic inflammatory disorder. In a preferred embodiment, the allergic inflammatory disorder is allergic rhinosinusitis, allergic asthma, allergic conjunctivitis, or atopic dermatitis.

The present invention provides methods for using engineered anti-TSLPR for the treatment and diagnosis of fibrosis, inflammatory bowel disease, Hodgkin's lymphoma, respiratory viral infections or other viral infections, rheumatoid arthritis, or any other disorder characterized by inflammation at the site of injury.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Example 1

General Methods

Standard methods in molecular biology are described (Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan et al. (2000) *Current Protocols in Protein Science, Vol.* 2, John Wiley and Sons, Inc., New York; Ausubel et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan et al. (2001) *Current 49A5 Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan et al. (2001) *Current Protocols in Immunology, Vol.* 4, John Wiley, Inc., New York).

Methods for flow cytometry, including fluorescence activated cell sorting (FACS), are available (see, e.g., Owens et al. (1994) *Flow Cytometry Principles for Clinical Laboratory Practice*, John Wiley and Sons, Hoboken, N.J.; Givan (2001) *Flow Cytometry, 2nd* ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Example 2

Generation of Mouse Anti-TSLPR Antibodies

Mouse antibodies against human TSLPR were produced according to the following protocol: five BALB/c mice were immunized in their right rear footpad with 5 micrograms of a hTSLPR-Ig fusion in 50 microliters of Corixa MPL+TDM adjuvant (Sigma M6535-1VL) on days 1, 7, 33, 48, 77, 85, 92 and 99. On day 109, cells from both popliteal and inguinal nodes were fused with myeloma cells (ATCC P3x63Ag8.653) using electrofusion.

The procedure resulted in the generation of approximately 28 hybridomas, including the hybridomas producing the mouse antibodies described in Tables 4 and 6. The hybridoma producing the mouse 13H5 antibody (designated LB55-13H, 5.2; C3) was deposited with the ATCC® (10801 University Boulevard, Manassas, Va. 20110-2209 USA) on Mar. 25, 2008, and received ATCC® Deposit Designation PTA-9111.

Generation of TSLPR-Ig fusion: TSLPR fragment was ligated into a CMVGFP adeno vector that already contained the C-terminal Ig and N-terminal flag. The TSLPR fragment was cloned in between these two regions using the HindIII site. This clone was transfected in HEK293 cells and TSLPR-Ig protein was affinity purified over a M2 anti-Flag antibody agarose column using standard procedures.

Example 3

Generation of Rat Anti-TSLPR Antibody LB 1.18B3

Rat antibodies against human TSLPR were produced according to the following protocol: One rat was immunized by intraperitoneal injection with 50 micrograms of a hTSLPR-Ig fusion in 1 ml of Complete Freund's Adjuvants and boosted 7 times with 25-50 micrograms of hTSLPR-Ig fusion in Incomplete Freund's Adjuvant subcutaneous and/or intraperitoneally at 14 day intervals. Cells from the spleen were fused with myeloma cells (ATCC P3x63Ag8.653) using PEG.

Example 4

Humanization of Anti-Human TSLPR Antibodies

The humanization of mouse anti-human TSLPR antibody 13H5 was performed as essentially as described in PCT patent application publications WO 2005/047324 and WO 2005/047326, which are incorporated by reference.

Variable light and heavy domains of the anti-TSLPR monoclonal antibody (13H5) were cloned and fused to a human kappa light chain (CL domain) and human IgG1 heavy chain (CH1-hinge-CH2-CH3), respectively.

The amino acid sequence of the non-human VH domain was compared to a group of three human VH germline amino acid sequences; one representative from each of subgroups IGHV1, IGHV3 and IGHV4. The VH subgroups are listed in M.-P. Lefranc, "Nomenclature of the Human Immunoglobulin Heavy (IGH) Genes", *Experimental and Clinical Immunogenetics*, 18:100-116, 2001. Mouse 13H5 antibody scored highest against human heavy chain germline IGHV3-30 in subgroup VH-III.

For the mouse 13H5, the VL sequence was of the kappa subclass of VL. The amino acid sequence of the non-human VL domain was compared to a group of four human VL kappa germline amino acid sequences. The group of four is comprised of one representative from each of four established human VL subgroups listed in V. Barbie & M.-P. Lefranc, "The Human Immunoglobulin Kappa Variable (IGKV) Genes and Joining (IGKJ) Segments", *Experimental and Clinical Immunogenetics*, 15:171-183, 1998 and M.-P. Lefranc, "Nomenclature of the Human Immunoglobulin Kappa (IGK) Genes", *Experimental and Clinical Immunogenetics*, 18:161-174, 2001. The four subgroups also correspond to the four subgroups listed in Kabat et al. "Sequences of Proteins of Immunological Interest", U.S. Department of Health and Human Services, NIH Pub. 91-3242, 5th Ed., 1991, pp. 103-130. Mouse 13H5 antibody scored highest against human light chain germline IGKV1-39 in subgroup VLk-1.

Once the target amino acid sequences of the variable heavy and light chains were determined, plasmids encoding the full-length humanized antibody were generated. Codon-optimized DNA encoding the humanized full-length human IgG1 heavy chain and full-length human kappa light chain were synthesized using a commercial vendor (GeneArt AG, Regensburg, Germany). The humanized heavy and light variable chain amino acid sequences, are set forth in SEQ ID NOs: 51 and 52. The full-length humanized heavy and light chain amino acid sequences, are set forth in SEQ ID NOs: 53 and 54. The nucleic acids encoding humanized heavy and light chain amino acid sequences are set forth in SEQ ID NO: 73 and 74.

Chimeric 13H5 antibodies, comprising the mouse variable regions and human constant regions were created; protein was generated and tested for binding. Testing demonstrated affinity comparable to the parental antibody. There is a glycosylation site at position 69 of SEQ ID NO:50. Glycosylation at this position is not required for binding of the antibody. Humanization of the antibody removed the glycosylation.

An IgG4 isotype of the above described hu13H5 antibody can be created by replacing the heavy chain constant region coding sequence for the human γ1 chain with that of a γ4 chain. A mutation (for example a point mutation at Ser241Pro based on Kabat numbering) can be introduced into the hinge region of the γ4 sequence to avoid formulation of half molecules when the antibody is expressed and produced in cell culture.

Mouse antibodies 70E8 and 54C11 can be humanized according to the procedures described above. Mouse 70E8 and 54C11 antibodies score the highest against human heavy chain germline IGHV1-8 in subgroup VHI. Mouse 70E8 and 54C11 antibodies score the highest against human chain germline IGKV4-1 in subgroup VL-IV. Exemplary humanized sequences for the variable regions of mouse 70E8 and 54C11 antibodies are provided in SEQ ID NOS: 57-58 and 61-62.

Example 5

Determining of $EC_{50}$ for Anti-Human TSLPR Antibodies Using ELISA

The ELISA measures the EC50 of certain mouse anti-TSLPR antibodies generated according to Example 2 are reported on Table 4. The antibodies were purified from hybridoma supernatants, and his-hTSLPR or cTSLPR-Ig was used to determine binding affinity.

Generation of his-hTSLPR: A hTSLPR-ECTO-His having the amino acid sequence of SEQ ID NO: 75 was ligated into the pCMV1 vector to yield pCMV1-hTSLPR-ECTO-RGS6XHis, was transiently transfected in HEK293F cells and purified from the cell culture medium using an IMAC column purchased fro GE Healthcare using standard procedures. Briefly, the column was equilibrated in five column volumes of 10 mM imidazole, 0.5 M sodium chloride, PBS pH 8.0. The culture medium was loaded into the IMAC column. The load was washed down in the same equilibration buffer. The bound material was eluted using a single step elution in 250 mM imidazole, 0.5 M sodium chloride, PBS, pH 8.0. The purified material was dialyzed in 20 mM sodium acetate, 7% sucrose, pH 5.5. The sample was filtered, protein concentration was determined with OD280 nm measurements. The sample was analyzed by SDS-PAGE and by SEC-HPLC.

Generation of cTSLPR-Ig: A NHP-TSLPR Fragment having the nucleic acid of SEQ ID NO: 76 and encoding the amino acid sequence of SEQ ID NO: 77 was ligated into the HindIII site of pCIF.V1 (preprotrypsin leader with N terminal flag and C terminal IgG in pCMV-1) vector to yield cTSLPR-Ig (Mam-Trans[FlagPreProTrypsin]DELTA2_NHP[Ig]). The vector was transiently transfected in HEK293F cells and the cTSLPR-IG protein was purified from the cell culture medium using a Protein A Sepharsoe column purchased from GE Healthcare. Briefly, 3 M NaCl was added to the supernatant. The pH was adjusted to 7.9-8.1 with 1M Tris pH 9.0. The buffers used for the purification are as follows:

Wash buffer: 4M NaCl with 50 mM borate, PH 8.0 (Buffer A)

Elution buffer: 0.1M Na Citrate, PH 3.0 (Buffer B)

The Protein A Sepharose column was equilibrated with 5 CV of Buffer A. The culture medium was loaded onto the Protein A column. The column was washed with 5-10 CV Buffer A., and the protein was eluted with 5-6 CV Buffer B. 1M Tris PH 9.0 was added to neutralize each fraction following elution, with a ratio of ~1:5 neutralizing buffer to fraction volume. The fractions were dialyzed versus 1×PBS. The sample was filtered, protein concentration was determined with OD280 nm measurements. The sample was analyzed by SDS-PAGE.

Materials:
  Nunc Maxisorp 96U well Immunoplate. (Nunc #449824)
  10× phosphate-buffered saline (PBS), pH 7.4 (Fisher # BP399-20)
  Tween-20, enzyme grade (Fisher # BP337-500)
  Albumin, bovine serum (Sigma # A2153)
  Coating Buffer: 1 µg/mL TSLP in PBS at 50 µL/well
Detection reagent: Goat anti-mouse IgG(H+ L)—Jackson ImmunoResearch—115-035-062
Substrate Solution: ABTS Peroxidase Substrate 1C (Kirkegaard & Perry Labs #50-66-00)
ELISA Diluent and Assay Buffer: PBS; 0.1% BSA; 0.05% Tween-20
ELISA Wash Buffer: PBS; 0.05% Tween-20
Equipment:
  Molecular Devices Scanwasher300™
  Molecular Devices VersaMax™ microplate reader
Protocol:
  Coating of plates was performed as follows: TSLPR (50 ng per well) in PBS was incubated at 4° C. overnight. Plates were washed with 1 cycle (3 washes/cycle) on a Molecular Devices plate washer. Antibody was then titrated across a row of eight wells in the range of 3000 ng/mL to 0.4572 ng/mL using serial 3-fold dilutions and incubated for 60 min. at 25° C. Plates were washed for 1 cycle, HRP-goat anti-mouse) (1:2,000 dilution) was added at 0.05 mL/well and incubated for 60 min at 25° C. Plates were washed for 1 cycles. ABTS substrate was added at 0.05 mL/well and incubated 10 min at 25 C. Plates read at) or $A_{405\ nm}$.

Table 4 shows the results of the ELISA analysis.

TABLE 4

$EC_{50}$ Values Determined By ELISA

| Hybridoma | Species | Isotype | His-hTSLPR ELISA - EC50 (ng/ml) | cTSLPR-Ig ELISA - EC50 (ng/ml) |
|---|---|---|---|---|
| LB55.61B3.2H12 | mouse | G1/k | 18.1 | 990.2 |
| LB55.70E8.1A8 | mouse | G1/k | 16.2 | 958 |
| LB55.54C11.3G11 | mouse | 2a/k | 5.9 | 153.2 |
| LB55.4G8.2A6 | mouse | G1/k | 5.9 | 81 |
| LB55.13H5.2C3 | mouse | G1/k | 10.6 | >1 |
| LB55.49A5.2F9 | mouse | G1/k | 41.7 | 5.9 |
| LB55.23A11.2F7 | mouse | G1/k | 8.1 | 55.4 |

TABLE 4-continued $EC_{50}$ Values Determined By ELISA

| Hybridoma | Species | Isotype | His-hTSLPR ELISA - EC50 (ng/ml) | cTSLPR-Ig ELISA - EC50 (ng/ml) |
|---|---|---|---|---|
| LB55.61C11.2B1 | mouse | 2a/k | 26 | 260.2 |
| LB55.9H6.3A5 | mouse | 2a/k | ND | ND |
| LB55.54A11.3D6 | mouse | 2a/k | 45.8 | 7.5 |
| LB55.45D12.3A4 | mouse | 2a/k | ND | ND |
| LB55.16C7.2A6 | mouse | 2a/k | ND | ND |
| LB55.30B10.2E11 | mouse | 2a/k | 71.3 | 474.9 |
| LB55.64E10.1B10 | mouse | 2a/k | 29 | 1184 |
| LB55.38E8.2H1 | mouse | G1/k | ND | ND |

The antibody generated by hybridoma LB18.22D5 was generated using cyno-TSLPR as an antigen. All other antibodies were generated using human-TSLPR as an antigen.

Example 6

Affinity of Anti-Human TSLPR Antibodies for Human and Cyno TSLP

The kinetic binding activities of the mouse anti human TSLPR antibody 13H5, chimeric anti-human TSLPR 13H5 antibody, rat anti-human TSLPR antibody 18B3, and mouse anti-human TSLPR antibody 70E8 against both human (hu) and cynomolgus monkey (cyno) TSLPR were measured by surface plasmon resonance using a BIAcore T100 system (BIAcore AB, Upsalla, Sweden). Approximately 70RUs of human TSLP or cyno TSLP were immobilized via amine coupling chemistry onto a Sensor Chip CM5 (Research grade, BR-1006-68). HBS-EP buffer (BR-1006-69) was used as the running buffer with a flow rate of 30 µL/min. Antibodies at varying concentrations ranging from 0.01 to 600 nM were injected over the immobilized hu or cyno TSLP surfaces at a flow rate of 30 µL/min. Following each injection cycle the CM5 chip surface was regenerated using a series of solutions (10 mM Glycine pH 1.5 and 25 mM NaOH respectively) at a flow rate of 75 µL/min.

Background subtraction binding sensorgrams were used for analyzing the rate constant of association (ka) and dissociation (kd), and the equilibrium dissociation constant $K_D$. The resulting data sets shown in Table 5 were fitted with a bivalent analyte model using the BIAevaluation software (version 1.0).

TABLE 5

BIAcore Analysis

| Antibody (Analyte) | Batch No. | n | Capture direct (CM5) | ka (1/Ms) (×10$^5$) | kd (1/s) (×10$^{-6}$) | KD (pM) | Rmax (RU) | Chi$^2$ |
|---|---|---|---|---|---|---|---|---|
| chim 13H5 | 52ABW | n = 2 | huTSLP R-hIg P405A | 13.4 | 136 | 102 | 20 | 0.7 |
| 13H5 | 55ABS | n = 6 | | 21.2 | 78 | 37 | 21 | 0.8 |
| 18B3 | PAB1380/46ABM | n = 2 | | 18.1 | 15 | 8 | 15 | 0.2 |
| 70E8 | 41ABW | n = 2 | | 15.2 | 120 | 79 | 21 | 0.8 |
| chim 13H5 | 52ABW | n = 2 | cyTSLP R-hIg P749 | 4.6 | 172 | 374 | 28 | 1.1 |
| 13H5 | 55ABS | n = 6 | | 8.0 | 71 | 89 | 27 | 1.0 |
| 18B3 | PAB1380/46ABM | n = 2 | | 7.7 | 7804 | 10135 | 13 | 0.2 |
| 70E8 | 41ABW | n = 2 | | No binding observed | | | | |

Example 7

Proliferation Bioassay for the Assessment of Neutralizing Anti-TSLPR Antibody

The ability of a monoclonal antibody to biologically neutralize TSLPR was assessed by the application of short-term proliferation bioassays that utilize cells which express recombinant human or non-human primate TSLP receptors. The transfectant Ba/F3-hTSLPR (Ba/F3-hTSLPR-hIL7Ra) cells and Ba/F3-cyTSLPR (Ba/F3-cTSLPR-cIL7Ra) proliferate in response to hTSLP or cTSLP respectively and the response can be inhibited by a neutralizing anti-TSLPR antibody. Each antibody was titrated against a concentration of TSLP chosen within the linear region of the TSLP dose-response curve, near plateau and above the TSLP $EC_{50}$. Proliferation, or lack thereof, is measured by colorimetric means using Alamar Blue, a growth indicator dye based on detection of metabolic activity. The ability of an antibody to neutralize TSLP is assessed by its EC50 value, or concentration of antibody that induces half-maximal inhibition of TSLP proliferation.

Ba/F3 transfectants are maintained in RPMI-1640 medium, 10% fetal calf serum, 50 µM 2-mercaptoethanol, 2 mM L-Glutamine, 50 µg/mL penicillin-streptomycin, and 10 ng/mL mouse IL-3.

Ba/F3 proliferation bioassays are performed in RPMI-1640 medium, 10% fetal calf serum, 50 µM 2-mercaptoethanol, 2 mM L-Glutamine, and 50 µg/mL penicillin-streptomycin.

The assay is performed in 96-well flat bottom plates (Falcon 3072 or similar). All preparations of reagents and cell suspensions utilize the appropriate bioassay medium. The assay volume is 150 μL per well. Titrations of an anti-hTSLPR antibody or anti-cTSLPR are pre-incubated with Ba/F3-hTSLPR cells or Ba/F3-cTSLPR cells respectively for 30-60 minutes at room temperature, hTSLPR (2 ng) or cTSLP (1 ng) is added to the wells following the antibody-cell pre-incubation. Bioassay plates are incubated in a humidified tissue culture chamber (37C, 5% $CO_2$) for 40-48 hours. At the end of the culture time, Alamar Blue (Biosource Cat #DAL1100) is added and allowed to develop for 8-12 hours. Absorbance is then read at 570 nm and 600 nm (VERSAmax Microplate Reader, Molecular Probes), and an $OD_{570-600}$ is obtained. Duplicates or triplicates are recommended.

Cells are used in a healthy growth state, generally at densities of $3-8\times10^5$/mL. Cells are counted, pelleted, washed twice in bioassay medium, and suspended to the appropriate density for plating.

TSLP was prepared to working concentration and added to first well at 75 μL. Serial dilutions of 1:3 were made by titrating 25:50 μL in bioassay medium across wells, leaving 50 μL/well. Cells were suspended to the appropriate density for plating at 100 μL per well.

The antibody was prepared to working concentration and added to the first well at 75 μL. Serial dilutions of 1:3 were made by titrating 25:50 μL in bioassay medium across wells, leaving 50 μL per well. Ba/F3 cells were suspended at the appropriate density for plating at 50 μL per well, and added to the wells containing the titrated antibody. TSLP at the appropriate concentration was added at 50 μL per well following the antibody-cell pre-incubation.

Using GraphPad Prism 3.0 software, absorbance was plotted against cytokine or antibody concentration and EC50 values were determined using non-linear regression (curve fit) of sigmoidal dose-response.

The assay results are shown in Table 6.

TABLE 6

Inhibition Of Proliferation

| | | Blocking Activity | | | | | | | | | |
|---|---|---|---|---|---|---|---|---|---|---|---|
| | | Ba/F3-huTSLPR | | | | | (Cross-Blocking) Ba/F3-cyTSLPR | | | | |
| | | Avg IC50 | SD | IC50 (ng/ml) | | | IC50 (ng/ml) | | | Avg IC50 | SD |
| Antibody | Batch No. | (ng/ml) | (ng/ml) | Assay I | Assay II | Assay III | Assay I | Assay II | Assay III | (ng/ml) | (ng/ml) |
| LB18.22D5 (xcyTSLPR) | PAB567 | not tested | not tested | not tested | not tested | not tested | 1200 | 1373 | 1061 | 1211 | 156 |
| LB55.13H5.2C3 | 19ABP | 12.1 | 2.2 | 12.7 | 14.0 | 9.7 | 10.4 | 14.8 | 13.4 | 12.9 | 2 |
| LB55.54C11.3G11 | 17ABP | 20.3 | 2.1 | 19.5 | 18.8 | 22.7 | not blocking | — | — | not blocking | — |
| LB55.70E8.1A8 | 16ABP | 44.6 | 4.1 | 44.2 | 48.9 | 40.7 | ~55K | ~90K | ~90K | >50K | — |
| LB55.23A11.2F7 | 21ABP | 89.8 | 9.5 | 97.1 | 93.3 | 79.1 | not blocking | — | — | not blocking | — |
| LB55.49A5.2F9 | 20ABP | 127 | 17.8 | 143 | 108 | 131 | 202 | 246 | 246 | 231 | 25 |
| LB55.61C11.2B1 | 22ABP | 162 | 19.7 | 174 | 139 | 172 | ~13K | ~18K | ~15K | >10K | — |
| LB55.54A11.3D6 | 26ABP | 178 | 41.1 | 211 | 132 | 191 | 125 | 153 | 137 | 138 | 14 |
| LB55.4G8.2A6 | 18ABP | 262 | 51.7 | 292 | 202 | 291 | not blocking | — | — | not blocking | — |
| LB1.18B3 (xhuTSLPR) | PAB506 | 304 | 39.9 | 318 | 259 | 335 | not tested | not tested | not tested | not tested | not tested |
| LB55.9H6.3A5 | 25ABP | 306 | 80.7 | 397 | 244 | 276 | not blocking | — | — | not blocking | — |
| LB55.16C7.2A6 | 28ABP | 348 | 84.7 | 413 | 252 | 378 | not blocking | — | — | not blocking | — |
| LB55.45D12.3A5 | 27ABP | 723 | 76.1 | 797 | 645 | 726 | not blocking | — | — | not blocking | — |
| LB55.38E8.2H1 | 44ABQ | 1661 | 486.1 | 2191 | 1556 | 1236 | | 1467 | 1158 | 1313 | 218 |

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

What is claimed is:

1. A binding compound that specifically binds human and cyno TSLPR comprising:
   an antibody heavy chain variable region, or TSLPR-binding fragment thereof, comprising the CDR-H1 sequence of SEQ ID NO:1, the CDR-H2 sequence of SEQ ID NO:2 or SEQ ID NO:73, and the CDR-H3 sequence of SEQ ID NO:3; and
   an antibody light chain variable region, or TSLPR-binding fragment thereof, comprising the CDR-L1 sequence of SEQ ID NO:4, the CDR-L2 sequence of SEQ ID NO:5, and the CDR-L3 sequence of SEQ ID NO:6 or SEQ ID NO:74.

2. The binding compound of claim 1, comprising:
   a heavy chain variable region comprising residues 1-116 of SEQ ID NO: 53 or of SEQ ID NO:51; and
   a light chain variable region comprising residues 1-108 of SEQ ID NO: 54 or of SEQ ID NO:52.

3. The binding compound of claim 1, wherein the binding compound is a TSLPR-binding antibody fragment selected from the group consisting of Fab, Fab', Fab'-SH, Fv, scFv, $F(ab')_2$, and a diabody.

4. A composition comprising the binding compound of claim 1 in combination with a pharmaceutically acceptable carrier or diluent.

* * * * *

```
                          SEQUENCE LISTING

<160> NUMBER OF SEQ ID NOS: 75

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 1

Gly Phe Ser Leu Ser Arg Tyr Gly Val His
1               5                   10

<210> SEQ ID NO 2
<211> LENGTH: 16
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 2

Val Ile Trp Arg Ser Gly Ser Thr Asp Tyr Asn Ala Ala Phe Met Ser
1               5                   10                  15

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 3

Lys Ala Phe Tyr Val Met Asp Tyr
1               5

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 4

Arg Ala Ser Gln Asp Ile Ser Ile Tyr Leu Asn
1               5                   10

<210> SEQ ID NO 5
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 5

Tyr Thr Ser Arg Leu His Ser
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 6

Gln Gln Gly Asn Thr Leu Pro Trp Thr
1               5

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 7

Asn Tyr Ser Ile Thr Ser Gly Tyr Ser Trp Pro
1               5                   10

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 8

Tyr Ile His Ser Ser Gly Arg Thr Asn Tyr Asn Pro Ser Leu Lys Ser
1               5                   10                  15

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 9

Ser Gln Leu Gly Leu Val Phe Phe Ala Tyr
1               5                   10

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"
```

```
<400> SEQUENCE: 10

Lys Ala Ser Gln Ser Val Gly Ala Asn Val Ala
1               5                   10

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 11

Ser Ala Ser Tyr Arg Phe Ser
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 12

Gln Gln Tyr Asn Ser Tyr Pro Tyr Thr
1               5

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 13

Gly Phe Thr Phe Thr Asp Tyr Ala Ile His
1               5                   10

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 14

Ile Ile Arg Pro Ser Asn Gly Asn Thr Asn Cys Asp Gln Lys Phe Lys
1               5                   10                  15

Asp

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 15
```

```
Ser Arg Val Trp Gly Gly Ser Leu Ala Tyr
1               5                   10

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 16

Lys Ala Ser Gln Asn Val Gly Thr Asn Ile Ala
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 17

Ser Ala Ser Tyr Arg Tyr Ser
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 18

Gln Gln Tyr Lys Ser Tyr Pro Trp Thr
1               5

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 19

Gly Phe Ser Leu Thr Thr Tyr Gly Val His
1               5                   10

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 20

Val Ile Trp Arg Gly Gly Asn Thr Ala Tyr Asn Pro Ala Phe Met Ser
1               5                   10                  15

<210> SEQ ID NO 21
```

```
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 21

Lys Ser Tyr Tyr Gly Tyr His Ala Met Gly Tyr
1               5                   10

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 22

Ala Ser Gln Asp Ile Ser Asn Tyr Leu Asn
1               5                   10

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 23

Tyr Thr Ser Arg Leu His Ser
1               5

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 24

Gln Gln Ala Asn Thr Leu Pro Trp Thr
1               5

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 25

Gly Phe Ser Leu Thr Ile Tyr Gly Leu His
1               5                   10

<210> SEQ ID NO 26
<211> LENGTH: 16
<212> TYPE: PRT
<213> ORGANISM: Artificial Sequence
<220> FEATURE:
<221> NAME/KEY: source
```

<223> OTHER INFORMATION: /note="Description of artificial sequence:
       Synthetic peptide"

<400> SEQUENCE: 26

Val Ile Trp Arg Gly Gly Ser Thr Asp Tyr Asn Ala Ala Phe Met Ser
1               5                   10                  15

<210> SEQ ID NO 27
<211> LENGTH: 13
<212> TYPE: PRT
<213> ORGANISM: Artificial Sequence
<220> FEATURE:
<221> NAME/KEY: source
<223> OTHER INFORMATION: /note="Description of artificial sequence:
       Synthetic peptide"

<400> SEQUENCE: 27

Pro Tyr Tyr Asp Tyr Asp Gly Asn Trp Tyr Phe Asp Val
1               5                   10

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
       Synthetic peptide"

<400> SEQUENCE: 28

Ala Ser Gln Asn Val Gly Thr Asn Val Ala
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
       Synthetic peptide"

<400> SEQUENCE: 29

Ser Ala Ser Ser His Cys Ser
1               5

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
       Synthetic peptide"

<400> SEQUENCE: 30

Gln Gln Tyr Asn Arg Tyr Pro Leu Thr
1               5

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
       Synthetic peptide"

<400> SEQUENCE: 31

```
Gly Tyr Ser Phe Thr Gly Tyr Tyr Ile His
1               5                   10
```

```
<210> SEQ ID NO 32
<211> LENGTH: 17
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 32

Arg Ile Asn Pro Tyr Asn Gly Ala Thr Ile Tyr Asn Pro Asn Phe Lys
1               5                   10                  15

Asp
```

```
<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 33

Ser Tyr Gly Tyr Val Asn Tyr Phe Asp Tyr
1               5                   10
```

```
<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 34

Ala Ser Gln Ser Ile Ser Asn Asn Leu His
1               5                   10
```

```
<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 35

Phe Gly Phe Gln Ser Ile Ser
1               5
```

```
<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 36

Gln Gln Thr Asn Ser Trp Leu Thr
1               5
```

```
<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 37

Gly Tyr Thr Phe Thr Ser Tyr Asn Leu His
1               5                   10

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 38

Tyr Ile Tyr Pro Gly Leu Asn Gly Thr Leu Tyr Asn Gln Lys Phe Arg
1               5                   10                  15

Gly

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 39

Ser Asp Tyr Gly Lys Ala Trp Phe Ala Tyr
1               5                   10

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 40

Ala Ser Gln Ser Ile Ala Thr Lys Ile His
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 41

Leu Gly Ser Glu Ser Ile Ser
1               5

<210> SEQ ID NO 42
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 42

Gln Gln Ser Asn Arg Tyr Pro Tyr Thr
1               5

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 43

Gly Phe Thr Phe Asn Asn Tyr Trp Met Thr
1               5                   10

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 44

Ser Ile Thr Asp Thr Ser Gly Arg Thr Tyr Tyr Pro Asp Ser Val Lys
1               5                   10                  15

Gly

<210> SEQ ID NO 45
<211> LENGTH: 8
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 45

Thr Leu Gly Gly Ile Pro Arg Asp
1               5

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 46

Gly Ser Gln Asn Ile Asn Asn Tyr Leu Ala
1               5                   10

<210> SEQ ID NO 47
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of artificial sequence:
      Synthetic peptide"

<400> SEQUENCE: 47

Lys Thr Asn Ile Leu Gln Thr
1               5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 48

Tyr Gln Phe Asn Asn Gly Phe Thr
1               5

<210> SEQ ID NO 49
<211> LENGTH: 116
<212> TYPE: PRT
<213> ORGANISM: Mus sp.

<400> SEQUENCE: 49

Gln Val Leu Leu Lys Gln Ser Gly Pro Ser Leu Val Gln Pro Ser Gln
1               5                   10                  15

Ser Leu Ser Ile Thr Cys Thr Val Ser Gly Phe Ser Leu Ser Arg Tyr
                20                  25                  30

Gly Val His Trp Val Arg Gln Ser Pro Gly Lys Gly Leu Glu Trp Leu
            35                  40                  45

Gly Val Ile Trp Arg Ser Gly Ser Thr Asp Tyr Asn Ala Ala Phe Met
        50                  55                  60

Ser Arg Leu Ser Ile Thr Gln Asp Asn Ser Lys Ser Gln Val Phe Phe
65                  70                  75                  80

Asn Met Asn Ser Leu Gln Ser Asp Asp Ser Ala Ile Tyr Tyr Cys Ala
                85                  90                  95

Lys Lys Ala Phe Tyr Val Met Asp Tyr Trp Gly Gln Gly Thr Ser Val
            100                 105                 110

Thr Val Ser Ser
        115

<210> SEQ ID NO 50
<211> LENGTH: 109
<212> TYPE: PRT
<213> ORGANISM: Mus sp.

<400> SEQUENCE: 50

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ile Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asn Phe Ser Leu Thr Ile Thr Asn Leu Glu Glu
65                  70                  75                  80

Glu Asp Ile Ala Thr Tyr Phe Cys Gln Gln Gly Asn Thr Leu Pro Trp
```

```
                85                  90                  95
Thr Phe Gly Gly Gly Thr Lys Leu Glu Ile Lys Arg Thr
                100                 105

<210> SEQ ID NO 51
<211> LENGTH: 116
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 51

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Ser Arg Tyr
                20                  25                  30

Gly Val His Trp Val Arg Gln Ala Pro Gly Lys Gly Leu Glu Trp Val
            35                  40                  45

Ala Val Ile Trp Arg Ser Gly Ser Thr Asp Tyr Asn Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Lys Ala Phe Tyr Val Met Asp Tyr Trp Gly Gln Gly Thr Leu Val
                100                 105                 110

Thr Val Ser Ser
        115

<210> SEQ ID NO 52
<211> LENGTH: 109
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr
                100                 105

<210> SEQ ID NO 53
<211> LENGTH: 116
<212> TYPE: PRT
<213> ORGANISM: Artificial Sequence
<220> FEATURE:
```

-continued

```
<221> NAME/KEY: source
<223> OTHER INFORMATION: /note="Description of artificial sequence:
      Synthetic polypeptide"
<220> FEATURE:
<221> NAME/KEY: VARIANT
<222> LOCATION: (24)..(24)
<223> OTHER INFORMATION: /replace="Val"
<220> FEATURE:
<221> NAME/KEY: misc_feature
<222> LOCATION: (24)..(24)
<223> OTHER INFORMATION: /note="Residue given in the sequence has no
      preference with respect to those in the annotations for said
      position"
<220> FEATURE:
<221> NAME/KEY: VARIANT
<222> LOCATION: (48)..(48)
<223> OTHER INFORMATION: /replace="Leu"
<220> FEATURE:
<221> NAME/KEY: VARIANT
<222> LOCATION: (49)..(49)
<223> OTHER INFORMATION: /replace="Gly"
<220> FEATURE:
<221> NAME/KEY: misc_feature
<222> LOCATION: (48)..(49)
<223> OTHER INFORMATION: /note="Residues given in the sequence have no
      preference with respect to those in the annotations for said
      positions"
<220> FEATURE:
<221> NAME/KEY: VARIANT
<222> LOCATION: (64)..(64)
<223> OTHER INFORMATION: /replace="Lys"
<220> FEATURE:
<221> NAME/KEY: misc_feature
<222> LOCATION: (64)..(64)
<223> OTHER INFORMATION: /note="Residue given in the sequence has no
      preference with respect to those in the annotations for said
      position"
<220> FEATURE:
<221> NAME/KEY: VARIANT
<222> LOCATION: (67)..(67)
<223> OTHER INFORMATION: /replace="Leu"
<220> FEATURE:
<221> NAME/KEY: misc_feature
<222> LOCATION: (67)..(67)
<223> OTHER INFORMATION: /note="Residue given in the sequence has no
      preference with respect to those in the annotations for said
      position"
<220> FEATURE:
<221> NAME/KEY: VARIANT
<222> LOCATION: (71)..(71)
<223> OTHER INFORMATION: /replace="Gln"
<220> FEATURE:
<221> NAME/KEY: misc_feature
<222> LOCATION: (71)..(71)
<223> OTHER INFORMATION: /note="Residue given in the sequence has no
      preference with respect to those in the annotations for said
      position"
<220> FEATURE:
<221> NAME/KEY: VARIANT
<222> LOCATION: (76)..(76)
<223> OTHER INFORMATION: /replace="Ser"
<220> FEATURE:
<221> NAME/KEY: misc_feature
<222> LOCATION: (76)..(76)
<223> OTHER INFORMATION: /note="Residue given in the sequence has no
      preference with respect to those in the annotations for said
      position"
<220> FEATURE:
<221> NAME/KEY: VARIANT
<222> LOCATION: (78)..(78)
<223> OTHER INFORMATION: /replace="Val"
<220> FEATURE:
<221> NAME/KEY: misc_feature
<222> LOCATION: (78)..(78)
<223> OTHER INFORMATION: /note="Residue given in the sequence has no
      preference with respect to those in the annotations for said
      position"
<220> FEATURE:
<221> NAME/KEY: VARIANT
<222> LOCATION: (97)..(97)
```

```
<223> OTHER INFORMATION: /replace="Lys"
<220> FEATURE:
<221> NAME/KEY: misc_feature
<222> LOCATION: (97)..(97)
<223> OTHER INFORMATION: /note="Residue given in the sequence has no
      preference with respect to those in the annotations for said
      position"
<220> FEATURE:
<221> NAME/KEY: VARIANT
<222> LOCATION: (111)..(111)
<223> OTHER INFORMATION: /replace="Ser"
<220> FEATURE:
<221> NAME/KEY: misc_feature
<222> LOCATION: (111)..(111)
<223> OTHER INFORMATION: /note="Residue given in the sequence has no
      preference with respect to those in the annotations for said
      position"

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Ser Arg Tyr
            20                  25                  30

Gly Val His Trp Val Arg Gln Ala Pro Gly Lys Gly Leu Glu Trp Val
        35                  40                  45

Ala Val Ile Trp Arg Ser Gly Ser Thr Asp Tyr Asn Ala Ala Phe Met
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Lys Ala Phe Tyr Val Met Asp Tyr Trp Gly Gln Gly Thr Leu Val
            100                 105                 110

Thr Val Ser Ser
        115

<210> SEQ ID NO 54
<211> LENGTH: 108
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"
<220> FEATURE:
<221> NAME/KEY: MOD_RES
<222> LOCATION: (70)..(70)
<223> OTHER INFORMATION: /replace="Asn"
<220> FEATURE:
<221> NAME/KEY: misc_feature
<222> LOCATION: (70)..(70)
<223> OTHER INFORMATION: /note="Residue given in the sequence has no
      preference with respect to those in the annotations for said
      position"
<220> FEATURE:
<221> NAME/KEY: MOD_RES
<222> LOCATION: (92)..(92)
<223> OTHER INFORMATION: /replace="Gln"
<220> FEATURE:
<221> NAME/KEY: misc_feature
<222> LOCATION: (92)..(92)
<223> OTHER INFORMATION: /note="Residue given in the sequence has no
      preference with respect to those in the annotations for said
      position"

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ile Tyr
```

```
                  20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 55
<211> LENGTH: 119
<212> TYPE: PRT
<213> ORGANISM: Mus sp.

<400> SEQUENCE: 55

Asp Val Gln Leu Gln Glu Ser Gly Pro Asp Leu Val Lys Pro Ser Gln
1               5                   10                  15

Ser Leu Ser Leu Thr Cys Thr Val Thr Asn Tyr Ser Ile Thr Ser Gly
            20                  25                  30

Tyr Ser Trp Pro Trp Ile Arg Gln Phe Pro Gly Asn Lys Leu Glu Trp
        35                  40                  45

Leu Gly Tyr Ile His Ser Ser Gly Arg Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Ser Gln Leu Gly Leu Val Phe Phe Ala Tyr Trp Gly Gln Gly
            100                 105                 110

Thr Leu Val Thr Val Ser Ala
        115

<210> SEQ ID NO 56
<211> LENGTH: 109
<212> TYPE: PRT
<213> ORGANISM: Mus sp.

<400> SEQUENCE: 56

Asp Ile Val Met Thr Gln Ser Gln Lys Phe Met Ser Thr Ser Val Gly
1               5                   10                  15

Asp Arg Val Ser Val Thr Cys Lys Ala Ser Gln Ser Val Gly Ala Asn
            20                  25                  30

Val Ala Trp Tyr Gln Gln Ile Pro Gly His Ser Pro Lys Val Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Arg Arg Thr
            100                 105

<210> SEQ ID NO 57
```

```
<211> LENGTH: 119
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Asn Tyr Ser Ile Thr Ser Gly
            20                  25                  30

Tyr Ser Trp Pro Trp Val Arg Gln Ala Pro Gly Lys Gly Leu Glu Trp
        35                  40                  45

Val Ala Tyr Ile His Ser Ser Gly Arg Thr Asn Tyr Asn Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gln Leu Gly Leu Val Phe Phe Ala Tyr Trp Gly Gln Gly
            100                 105                 110

Thr Leu Val Thr Val Ser Ser
        115

<210> SEQ ID NO 58
<211> LENGTH: 108
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Gly Ala Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Val Glu Ile Lys Arg
            100                 105

<210> SEQ ID NO 59
<211> LENGTH: 119
<212> TYPE: PRT
<213> ORGANISM: Mus sp.

<400> SEQUENCE: 59

Gln Val Gln Leu Gln Gln Ser Gly Pro Glu Val Val Arg Pro Gly Val
1               5                   10                  15

Ser Val Lys Ile Ser Cys Lys Gly Ser Gly Phe Thr Phe Thr Asp Tyr
            20                  25                  30
```

```
Ala Ile His Trp Val Arg Gln Ser His Ala Lys Ser Leu Glu Trp Ile
        35                  40                  45

Gly Ile Ile Arg Pro Ser Asn Gly Asn Thr Asn Cys Asp Gln Lys Phe
    50                  55                  60

Lys Asp Lys Ala Thr Met Thr Val Asp Lys Ser Ser Thr Ala Tyr
65                  70                  75                  80

Leu Asp Leu Ala Arg Leu Thr Ser Glu Asp Ser Ala Ile Tyr Tyr Cys
                85                  90                  95

Ser Arg Ser Arg Val Trp Gly Gly Ser Leu Ala Tyr Trp Gly Gln Gly
            100                 105                 110

Thr Leu Val Thr Val Ser Ala
        115

<210> SEQ ID NO 60
<211> LENGTH: 109
<212> TYPE: PRT
<213> ORGANISM: Mus sp.

<400> SEQUENCE: 60

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Ile Ala Trp Tyr Gln Gln Lys Pro Gly Gln Ser Pro Glu Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Lys Ser Tyr Pro Trp
                85                  90                  95

Thr Phe Gly Gly Gly Thr Lys Leu Glu Ile Lys Arg Thr
            100                 105

<210> SEQ ID NO 61
<211> LENGTH: 119
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asp Tyr
            20                  25                  30

Ala Ile His Trp Val Arg Gln Ala Pro Gly Lys Gly Leu Glu Trp Val
        35                  40                  45

Ala Ile Ile Arg Pro Ser Asn Gly Asn Thr Asn Cys Asp Gln Lys Phe
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Val Trp Gly Gly Ser Leu Ala Tyr Trp Gly Gln Gly
            100                 105                 110
```

Thr Leu Val Thr Val Ser Ser
        115

<210> SEQ ID NO 62
<211> LENGTH: 108
<212> TYPE: PRT
<213> ORGANISM: Artificial Sequence
<220> FEATURE:
<221> NAME/KEY: source
<223> OTHER INFORMATION: /note="Description of artificial sequence:
      Synthetic polypeptide"

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Ile Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Pro Trp
                85                  90                  95

Thr Phe Gly Gln Gly Thr Lys Val Glu Ile Lys Arg
            100                 105

<210> SEQ ID NO 63
<211> LENGTH: 119
<212> TYPE: PRT
<213> ORGANISM: Mus sp.

<400> SEQUENCE: 63

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Asn Thr Ala Tyr Asn Pro Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr His Cys Ala
                85                  90                  95

Lys Lys Ser Tyr Tyr Gly Tyr His Ala Met Gly Tyr Trp Gly Gln Gly
            100                 105                 110

Thr Ser Val Thr Val Ser Ser
        115

<210> SEQ ID NO 64
<211> LENGTH: 109
<212> TYPE: PRT
<213> ORGANISM: Mus sp.

<400> SEQUENCE: 64

Asp Ile Gln Met Thr Gln Thr Thr Ser Ser Leu Ser Ala Ser Leu Gly
1               5                   10                  15

```
Asp Arg Val Thr Ile Asn Cys Arg Ala Ser Gln Asp Ile Ser Asn Tyr
            20                  25                  30

Leu Asn Trp Tyr Gln Gln Asn Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Ala Asn Thr Leu Pro Trp
                85                  90                  95

Thr Phe Gly Gly Gly Thr Lys Leu Glu Ile Lys Arg Thr
            100                 105
```

<210> SEQ ID NO 65
<211> LENGTH: 121
<212> TYPE: PRT
<213> ORGANISM: Mus sp.

<400> SEQUENCE: 65

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ile Tyr
            20                  25                  30

Gly Leu His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Arg Ile Thr Lys Asp Asn Ser Lys Ser Gln Val Phe Phe
65                  70                  75                  80

Lys Met Asp Ser Leu Gln Ala Asp Asp Thr Ala Ile Tyr Tyr Cys Ala
                85                  90                  95

Lys Pro Tyr Tyr Asp Tyr Asp Gly Asn Trp Tyr Phe Asp Val Trp Gly
            100                 105                 110

Ala Gly Thr Thr Val Thr Val Ser Ser
        115                 120
```

<210> SEQ ID NO 66
<211> LENGTH: 109
<212> TYPE: PRT
<213> ORGANISM: Mus sp.

<400> SEQUENCE: 66

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Lys Lys Ser Gly Gln Ser Pro Lys Pro Leu Ile
        35                  40                  45

Tyr Ser Ala Ser Ser His Cys Ser Glu Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Arg Tyr Pro Leu
                85                  90                  95

Thr Phe Gly Thr Gly Thr Lys Leu Glu Val Arg Arg Thr
            100                 105
```

-continued

```
<210> SEQ ID NO 67
<211> LENGTH: 119
<212> TYPE: PRT
<213> ORGANISM: Mus sp.

<400> SEQUENCE: 67

Glu Val Gln Leu Gln Gln Ser Gly Pro Glu Leu Val Lys Pro Arg Ala
1               5                   10                  15

Ser Val Lys Ile Ser Cys Lys Ala Ser Gly Tyr Ser Phe Thr Gly Tyr
            20                  25                  30

Tyr Ile His Trp Val Lys Gln Ser His Val Lys Ser Leu Glu Trp Ile
        35                  40                  45

Gly Arg Ile Asn Pro Tyr Asn Gly Ala Thr Ile Tyr Asn Pro Asn Phe
    50                  55                  60

Lys Asp Lys Ala Ser Leu Thr Val Asp Lys Ser Ser Thr Ala Phe
65                  70                  75                  80

Met Glu Val His Ser Leu Thr Ser Glu Asp Ser Ala Val Tyr Tyr Cys
                85                  90                  95

Ala Arg Ser Tyr Gly Tyr Val Asn Tyr Phe Asp Tyr Trp Gly Gln Gly
            100                 105                 110

Thr Thr Leu Thr Val Ser Ser
        115

<210> SEQ ID NO 68
<211> LENGTH: 108
<212> TYPE: PRT
<213> ORGANISM: Mus sp.

<400> SEQUENCE: 68

Glu Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr His Gln Lys Ser His Glu Ser Pro Arg Leu Leu Ile
        35                  40                  45

Lys Phe Gly Phe Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Thr Asn Ser Trp Leu Thr
                85                  90                  95

Phe Gly Ala Gly Thr Lys Leu Glu Leu Lys Arg Thr
            100                 105

<210> SEQ ID NO 69
<211> LENGTH: 119
<212> TYPE: PRT
<213> ORGANISM: Mus sp.

<400> SEQUENCE: 69

Gln Ala Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Tyr
            20                  25                  30

Asn Leu His Trp Ile Lys Leu Thr Pro Gly Gln Gly Leu Glu Trp Ile
        35                  40                  45

Gly Tyr Ile Tyr Pro Gly Leu Asn Gly Thr Leu Tyr Asn Gln Lys Phe
    50                  55                  60
```

```
Arg Gly Lys Ala Thr Leu Thr Ala Asp Thr Ser Ser Thr Ala Tyr
 65                  70                  75                  80

Met Gln Ile Ser Ser Leu Thr Ser Glu Asp Ser Ala Val Tyr Phe Cys
                 85                  90                  95

Ala Arg Ser Asp Tyr Gly Lys Ala Trp Phe Ala Tyr Trp Gly Arg Gly
            100                 105                 110

Thr Leu Val Thr Val Ser Ala
        115
```

<210> SEQ ID NO 70
<211> LENGTH: 109
<212> TYPE: PRT
<213> ORGANISM: Mus sp.

<400> SEQUENCE: 70

```
Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Ser Ile Ala Thr Lys
                 20                  25                  30

Ile His Trp Tyr Gln Gln Arg Thr Asp His Ser Pro Arg Leu Leu Ile
             35                  40                  45

Gln Leu Gly Ser Glu Ser Ile Ser Gly Ile Pro Ser Arg Phe Ser Gly
 50                  55                  60

Ser Gly Ser Gly Thr Asp Phe Thr Phe Thr Ile Asn Ser Val Glu Ser
 65                  70                  75                  80

Glu Asp Ile Ala Val Tyr Tyr Cys Gln Gln Ser Asn Arg Tyr Pro Tyr
                 85                  90                  95

Thr Phe Gly Gly Gly Thr Lys Leu Glu Val Lys Arg Thr
            100                 105
```

<210> SEQ ID NO 71
<211> LENGTH: 117
<212> TYPE: PRT
<213> ORGANISM: Rattus sp.

<400> SEQUENCE: 71

```
Glu Val Gln Leu Val Glu Ser Gly Gly Gly Leu Val Gln Pro Gly Arg
  1               5                  10                  15

Ser Leu Arg Leu Ser Cys Val Ala Ser Gly Phe Thr Phe Asn Asn Tyr
                 20                  25                  30

Trp Met Thr Trp Val Arg Gln Ala Pro Gly Lys Gly Leu Glu Trp Val
             35                  40                  45

Ala Ser Ile Thr Asp Thr Ser Gly Arg Thr Tyr Tyr Pro Asp Ser Val
 50                  55                  60

Lys Gly Arg Phe Thr Ile Ser Arg Asp His Ala Lys Ser Thr Leu Tyr
 65                  70                  75                  80

Leu Gln Met Asn Ser Leu Arg Pro Glu Asp Thr Ala Thr Tyr Tyr Cys
                 85                  90                  95

Thr Lys Thr Leu Gly Gly Ile Pro Arg Asp Trp Gly Gln Gly Val Met
            100                 105                 110

Val Thr Val Ser Ser
        115
```

<210> SEQ ID NO 72
<211> LENGTH: 108
<212> TYPE: PRT
<213> ORGANISM: Rattus sp.

<400> SEQUENCE: 72

```
Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Phe Lys Thr Asn Ile Leu Gln Thr Gly Ile Pro Leu Arg Phe Ser Gly
    50                  55                  60

Ser Gly Ser Gly Thr Asp Tyr Thr Leu Thr Ile Ser Ser Leu His Cys
65              70                  75                  80

Glu Asp Leu Ala Thr Tyr Tyr Cys Tyr Gln Phe Asn Asn Gly Phe Thr
                85                  90                  95

Phe Gly Pro Gly Thr Lys Leu Glu Leu Lys Arg Thr
            100                 105

<210> SEQ ID NO 73
<211> LENGTH: 16
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 73

Val Ile Trp Arg Ser Gly Ser Thr Asp Tyr Asn Ala Ala Phe Lys Ser
1               5                   10                  15

<210> SEQ ID NO 74
<211> LENGTH: 9
<212> TYPE: PRT
<213> ORGANISM: Artificial Sequence
<220> FEATURE:
<221> NAME/KEY: source
<223> OTHER INFORMATION: /note="Description of artificial sequence:
      Synthetic peptide"

<400> SEQUENCE: 74

Gln Gln Gly Gln Thr Leu Pro Trp Thr
1               5

<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of artificial sequence:
      Synthetic 6xHis tag"

<400> SEQUENCE: 75

His His His His His His
1               5
```